United States Patent
Friedhoff

(10) Patent No.: US 9,561,233 B2
(45) Date of Patent: Feb. 7, 2017

(54) USE OF IBOGAINE FOR THE TREATMENT OF PAIN

(71) Applicant: DemeRX, Inc., Fort Lauderdale, FL (US)

(72) Inventor: Lawrence Friedhoff, Fort Lauderdale, FL (US)

(73) Assignee: DEMERX, INC., Fort Lauderdale, FL (US)

( * ) Notice: Subject to any disclaimer, the term of this patent is extended or adjusted under 35 U.S.C. 154(b) by 0 days.

(21) Appl. No.: 14/635,929

(22) Filed: Mar. 2, 2015

(65) Prior Publication Data

US 2015/0258113 A1    Sep. 17, 2015

Related U.S. Application Data

(60) Provisional application No. 61/952,740, filed on Mar. 13, 2014.

(51) Int. Cl.
*A01N 43/00* (2006.01)
*A61K 31/55* (2006.01)
*A61K 31/00* (2006.01)

(52) U.S. Cl.
CPC .............. *A61K 31/55* (2013.01); *A61K 31/00* (2013.01)

(58) Field of Classification Search
None
See application file for complete search history.

(56) References Cited

U.S. PATENT DOCUMENTS

| | | | |
|---|---|---|---|
| 2,817,623 | A | 12/1957 | Schneider |
| 3,715,361 | A | 2/1973 | Epstein et al. |
| 4,499,096 | A | 2/1985 | Lotsof |
| 4,626,539 | A | 12/1986 | Aungst et al. |
| 4,806,341 | A | 2/1989 | Chien et al. |
| 4,857,523 | A | 8/1989 | Lotsof |
| 5,026,697 | A | 6/1991 | Lotsof |
| 5,149,538 | A | 9/1992 | Granger et al. |
| 5,152,994 | A | 10/1992 | Lotsof |
| 5,616,575 | A | 4/1997 | Efange et al. |
| 5,925,634 | A * | 7/1999 | Olney .................. A61K 31/135 514/214.03 |
| 7,638,651 | B2 | 12/2009 | Gant et al. |
| 8,362,007 | B1 | 1/2013 | Mash et al. |
| 8,367,693 | B1 | 2/2013 | King et al. |
| 8,741,891 | B1 | 6/2014 | Mash |
| 2003/0153552 | A1 | 8/2003 | Mash et al. |
| 2003/0199439 | A1 | 10/2003 | Simon |
| 2005/0022270 | A1 | 1/2005 | Hildebrand et al. |
| 2005/0148673 | A1 | 7/2005 | Harbut et al. |
| 2005/0203011 | A1 | 9/2005 | Ron |
| 2005/0222270 | A1 | 10/2005 | Olney et al. |
| 2006/0128610 | A1 | 6/2006 | Cooper |
| 2008/0234257 | A1 | 9/2008 | Gant et al. |
| 2008/0280886 | A1 | 11/2008 | Gant et al. |
| 2009/0082388 | A1 | 3/2009 | Hacksell et al. |
| 2009/0098069 | A1 | 4/2009 | Vacca |
| 2009/0252786 | A1 | 10/2009 | Hanz |
| 2009/0258869 | A1 | 10/2009 | Ron et al. |
| 2015/0231146 | A1 | 8/2015 | Friedhoff |
| 2015/0246055 | A1 | 9/2015 | Friedhoff |
| 2015/0257667 | A1 | 9/2015 | Friedhoff |
| 2015/0258104 | A1 | 9/2015 | Friedhoff |
| 2015/0258109 | A1 | 9/2015 | Maillet et al. |
| 2015/0258110 | A1 | 9/2015 | Maillet et al. |
| 2015/0258111 | A1 | 9/2015 | Maillet et al. |
| 2015/0258112 | A1 | 9/2015 | Friedhoff |
| 2016/0074414 | A1 | 3/2016 | Maillet |

FOREIGN PATENT DOCUMENTS

| | | | |
|---|---|---|---|
| BE | 664377 | | 5/1965 |
| BE | 806438 | | 2/1974 |
| DE | 19 02 227 | | 9/1969 |
| DE | 24 10 651 | | 9/1974 |
| DE | 24 50 188 | | 5/1975 |
| DE | 20 2008 007 923 U1 | | 10/2008 |
| WO | WO-91/18609 A1 | | 12/1991 |
| WO | WO-97/29735 | | 8/1997 |
| WO | WO-00/17366 | | 3/2000 |
| WO | WO-01/52851 | | 7/2001 |
| WO | WO-03/066029 A2 | | 8/2003 |
| WO | WO-03/066030 | | 8/2003 |
| WO | WO-2005/079767 | | 9/2005 |
| WO | WO-2008/039179 | | 4/2008 |
| WO | WO-2012/019106 | | 2/2012 |
| WO | WO-2013/063673 | | 5/2013 |
| WO | WO-2015/134405 | | 9/2015 |
| WO | WO2015/163844 | * | 10/2015 ........... C07D 487/04 |

OTHER PUBLICATIONS

Alper, K. R. et al., 'Treatment of acute opioid withdrawal with ibogaine', The American Journal on Addictions, 1999, vol. 8, No. 3, pp. 234-242. See abstract: and pp. 237 and 238.
Büchi, et al. "Chemical Transformations of Ibogaine," (1966), J. Am. Chem Society, 88(13), 3099-3109.
ISR and Written Opinion issued on PCT/US2015/018356, mailed May 20, 2015.
Rezvani, A. H. et al., 'Attenuation of alcohol intake by ibogaine in three strains of alcohol-preferring rats', Pharmacology Biochemistry and Behavior, 1995, vol. 52, No. 3, pp. 615-620. See abstract: and pp. 615 and 616.
Buchi et al., "Chemical Transformations of Ibogaine," Journal of the American Chemical Sociaty, vol. 88, Jun. 5, 1966, pp. 2532-2535.
Buchi et al., The Total Synthesis of Iboga Alkaloids, 1996, J Am Chem Society, Jul. 5, 1996, 88:13, pp. 3099- 3109.
Fermini et al., Nature Reviews Drug Discovery 2003, 2, pp. 439-447.

(Continued)

*Primary Examiner* — Jeffrey H Murray
(74) *Attorney, Agent, or Firm* — Foley & Lardner LLP

(57) ABSTRACT

This invention is directed to methods of treating pain in patients comprising treating patients with ibogaine, an ibogaine derivative, or a pharmaceutically acceptable salt and/or solvate thereof at a therapeutic dosage that provides an average serum concentration of about 50 ng/mL to about 850 ng/mL.

6 Claims, No Drawings

(56) References Cited

OTHER PUBLICATIONS

Hoelen et al., Long-Qt Syndrome Induced by the Antiaddiction Drug Ibogaine, Jan. 15, 2009, N. Engl J Med, 360(3) pp. 308-309.
Krantz et al., "Annals of Internal Medicine," publ. 2009, vol. 150, pp. 387-395.
Lotsof and Wachtel, "Manual for Ibogaine Therapy: Screening, Safety, Monitoring & Aftercare," 2d revision, 2003, www.ibogainedeskl.nl/manual.html.
Malik et al., "Evaluation of drug-induced QT interval prolongation: implications for drug approval and labelling," Drug Safety, Adis International Ltd., vol. 24(5), pp. 323-351 (2001).

\* cited by examiner

USE OF IBOGAINE FOR THE TREATMENT OF PAIN

CROSS-REFERENCE TO RELATED APPLICATIONS

This application claims benefit from U.S. Provisional Application No. 61/952,740, filed Mar. 13, 2014, which is hereby incorporated by reference in its entirety.

FIELD OF THE INVENTION

This invention is directed to methods of treating pain in patients comprising treating patients with ibogaine, an ibogaine derivative, or a pharmaceutically acceptable salt and/or solvate thereof at a therapeutic dosage that provides both an average serum concentration of about 50 ng/mL to about 850 ng/mL, including under conditions where the QT interval prolongation does not exceed about 50 milliseconds.

STATE OF THE ART

Pain is broadly defined as an unpleasant sensory experience associated with actual or potential tissue damage, or described in terms of such damage. The interpretation of sensory pain occurs when peripheral nerve endings called nociceptors are stimulated and subsequently transmit signals through sensory neurons in the spinal cord. The signals are then transmitted to the brain, at which point the individual becomes aware of the pain.

There are a number of pain categories and classifications, which for example, can be grouped into four categories according to the source and related nociceptors: (1) cutaneous pain; (2) somatic pain; (3) visceral pain; and (4) neuropathic pain. Other pain classifications include acute pain and chronic pain. Acute pain is defined as short-term pain or pain with an easily identifiable cause. Acute pain indicates present damage to tissue or disease and may be "fast" and "sharp" followed by aching pain. Acute pain is centralized in one area before becoming somewhat spread out. Acute pain generally responds well to medications (e.g., morphine).

Chronic pain may be medically defined as pain that has lasted six months or longer. This constant or intermittent pain has often outlived its purpose because it does not help the body to prevent injury. It is often more difficult to treat than acute pain. Expert care is generally necessary to treat any pain that has become chronic. In addition, stronger medications are typically used for extended periods in an attempt to control the pain. This can lead to drug dependency. For example, opioids are used in some instances for prolonged periods to control chronic pain. Drug tolerance, chemical dependency, and even psychological addiction may occur.

Debilitating chronic pain affects tens of millions of people annually. Accordingly, this costs hundreds of millions of dollars in terms of medication, physical therapy, and lost production. The current methods for treating chronic pain have a limited success rate and in some cases may result in chemical dependency.

Numerous treatments have been developed in attempts to ameliorate pain in its various categories. However, in many cases, treatment requires the use of addictive or habit-forming substances (e.g., morphine or methadone).

Accordingly, there is a significant need for an effective, non-addictive treatment for pain, such as chronic, debilitating, nociceptive pain, that reduces the need for habit-forming pain relieving drugs.

SUMMARY

Ibogaine has been used as a botanical preparation from the root bark of iboga tabernathe for over 100 years both as a crude preparation and as semisynthetic ibogaine, which was marketed in France until about 1970. High doses of ibogaine have been suggested to be useful as a treatment for pain and other conditions. However, the use of such high doses of ibogaine is associated with hallucinations and other negative side effects. In the United States, ibogaine is classified as a Schedule I controlled substance.

While ibogaine has been disclosed for treatment of substance addiction, its use in humans is complicated by the fact that the ranges in the prior art are exceptionally broad (0.01 to 1000 mg/kg body weight). Furthermore, human clinical studies demonstrate that the lower dosing of ibogaine has minimal impact on the alleviation of pain in patients. Thus, the previously disclosed broad range has now been found to be insufficient for human therapy at the lower end of this range.

It has been discovered that the use of ibogaine imparts a dose dependent prolongation of the treated patient's QT interval, rendering higher dosing of ibogaine unacceptable. A prolonged QT interval is a marker of potential Torsades de Pointes, a serious arrhythmia that can result in death.

The current invention is predicated on the surprising discovery that treatment with a narrow dosage range of ibogaine, an ibogaine derivative, or a pharmaceutically acceptable salt and/or solvate thereof between greater than about 0.1 mg/kg body weight and about 8 mg/kg body weight, provides a therapeutic alleviation of pain. Preferably, the dose range that provides both therapeutic results and an acceptable QT interval prolongation of less than 50 milliseconds in humans is between about 0.1 mg per kg body weight and no more than about 3 mg per kg body weight and, more preferably between about 0.7 mg per kg body weight and no more than about 2 mg per kg body weight, or any subrange or subvalue within the aforementioned ranges.

In a preferred embodiment, the narrow therapeutic doses of ibogaine, an ibogaine derivative, or a pharmaceutically acceptable salt and/or solvate thereof described above do not prolong the QT interval to unacceptable levels in human patients. In some embodiments, patients are administered therapeutic doses of ibogaine, an ibogaine derivative, or a pharmaceutically acceptable salt and/or solvate thereof in a clinical setting with cardiac monitoring. In some embodiments, the patient will be pre-screened to evaluate tolerance for prolongation of QT interval, e.g., to determine whether the patient has any pre-existing cardiac conditions which would disqualify them from treatment with ibogaine, an ibogaine derivative, or a pharmaceutically acceptable salt and/or solvate thereof. In one embodiment, a patient who exhibits a QT interval prolongation of less than about 20 ms after treatment with one or more therapeutic doses of ibogaine, an ibogaine derivative, or a pharmaceutically acceptable salt and/or solvate thereof will not require further clinical monitoring. In one embodiment, the patient is not monitored after administration of ibogaine, an ibogaine derivative, or a pharmaceutically acceptable salt and/or solvate thereof.

In some embodiments, the therapeutic dose of ibogaine, an ibogaine derivative, or a pharmaceutically acceptable salt and/or solvate thereof administered to the patient is sufficient to provide an average serum concentration of about 50 ng/mL to about 850 ng/mL, or any subrange or subvalue there between. In a preferred embodiment, the dose of ibogaine, an ibogaine derivative, or a pharmaceutically acceptable salt and/or solvate thereof administered to the patient provides an average serum concentration of about 50 ng/mL to about 400 ng/mL.

In some embodiments, the dose of ibogaine, an ibogaine derivative, or a pharmaceutically acceptable salt and/or solvate thereof that provides an average serum concentration of about 50 ng/mL to about 850 ng/mL is administered as a single dose. In some embodiments, the dose of ibogaine, an ibogaine derivative, or a pharmaceutically acceptable salt and/or solvate thereof that provides an average serum concentration of about 50 ng/mL to about 850 ng/mL is administered as multiple doses. In some embodiments, the aggregate dose of ibogaine, an ibogaine derivative, or a pharmaceutically acceptable salt and/or solvate thereof is from about 0.1 mg/kg to about 8 mg/kg. In a preferred embodiment, the aggregate dose of ibogaine, an ibogaine derivative, or a pharmaceutically acceptable salt and/or solvate thereof is from about 0.1 mg/kg to about 3 mg/kg. In another preferred embodiment, the aggregate dose of ibogaine, an ibogaine derivative, or a pharmaceutically acceptable salt and/or solvate thereof is from about 0.7 mg/kg to 1.5 mg/kg.

Compounds Administered

In the various method, formulation and kit aspects and embodiments, in one embodiment a compound utilized herein is represented by, or ibogaine as used herein is replaced by, a compound Formula I:

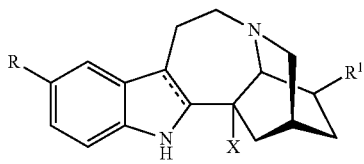

I or a pharmaceutically acceptable salt and/or solvate thereof, wherein

R is H, halo, $C_1$-$C_3$ alkyl, substituted $C_1$-$C_3$ alkyl, $OR^{10}$, $NH_2$, $NHR^{10}$, $NR^{10}R^{11}$, $NHC(O)R^{10}$, or $NR^{10}C(O)R^{11}$;

$R^1$ is H, $C_1$-$C_3$ alkyl, substituted $C_1$-$C_3$ alkyl, $C_1$-$C_3$ alkoxy, $CH_2$—X—$CH_3$, or $(CH_2)_m R^3$;

$R^2$ is H, COOH, $COOR^4$, $(CH_2)_n OH$, $CH(OH)R^5$, $CH_2OR^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;

$R^3$ is $C_1$-$C_3$ alkyl, benzyl, substituted $C_1$-$C_3$ alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, $O(CH_2)_p O(CH_2)_q O(CH_2)_r CH_3$ or $NR^8C(O)R^9$;

$R^4$ is $C_1$-$C_6$ alkyl or $(CH_2CH_2O)_n CH_3$;

$R^5$, $R^6$, $R^7$, $R^8$, $R^9$, $R^{10}$, and $R^{11}$ are independently alkyl or substituted alkyl;

$R^{12}$ is H, alkyl, or substituted alkyl;

$R^{13}$ is H, $OR^{10}$, alkyl, or substituted alkyl;

X is O or NH;

Y is O or S;

m is an integer selected from 0-8;

each of n, p and q is 1, 2 or 3; and r is 0, 1 or 2.

In another embodiment, the ibogaine derivative is represented by Formula Ii:

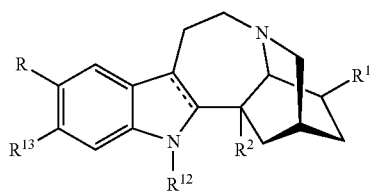

Ii or a pharmaceutically acceptable salt and/or solvate thereof, wherein

R is H, halo, $C_1$-$C_3$ alkyl, substituted $C_1$-$C_3$ alkyl, $OR^{10}$, $NH_2$, $NHR^{10}$, $NR^{10}R^{11}$, $NHC(O)R^{10}$, or $NR^{10}C(O)R^{11}$;

$R^1$ is H, $C_1$-$C_3$ alkyl, substituted $C_1$-$C_3$ alkyl, $C_1$-$C_3$ alkoxy, $CH_2$—X—$CH_3$, or $(CH_2)_m R^3$;

$R^2$ is H, COOH, $COOR^4$, $(CH_2)_n OH$, $CH(OH)R^5$, $CH_2OR^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;

$R^3$ is $C_1$-$C_3$ alkyl, benzyl, substituted $C_1$-$C_3$ alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, $O(CH_2)_p O(CH_2)_q O(CH_2)_r CH_3$ or $NR^8C(O)R^9$;

$R^4$ is $C_1$-$C_6$ alkyl or $(CH_2CH_2O)_n CH_3$;

$R^5$, $R^6$, $R^7$, $R^8$, $R^9$, $R^{10}$, and $R^{11}$ are independently alkyl or substituted alkyl;

$R^{12}$ is H, alkyl, or substituted alkyl;

$R^{13}$ is H, $OR^{10}$, alkyl, or substituted alkyl;

X is O or NH;

Y is O or S;

m is an integer selected from 0-8;

each of n, p and q is 1, 2 or 3; and r is 0, 1 or 2.

In one embodiment, the compound is of Formula IA:

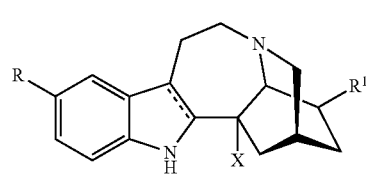

IA wherein

R is hydrogen or $C_1$-$C_3$-alkoxy, $R^1$ is hydrogen, $C_1$-$C_3$-alkyl, $C_1$-$C_3$ alkoxy, or $CH_2$—Y—$CH_3$ where Y is O or NH, and X is H, COOH, or $COOR^2$, where $R^2$ is $C_1$-$C_6$ alkyl or $(CH_2CH_2O)_n CH_3$, where n=1 to 3.

In one embodiment a compound utilized herein is represented by, or ibogaine as used herein is replaced by, a compound Formula II:

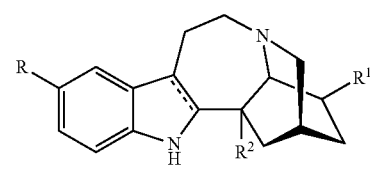

II or a pharmaceutically acceptable salt and/or solvate thereof, wherein

R is hydrogen or $C_1$-$C_3$ alkoxy;

$R^1$ is hydrogen, $C_1$-$C_3$ alkyl, $C_1$-$C_3$ alkoxy, $(CH_2)_m OC(O)$ alkyl, $(CH_2)_m OH$, $(CH_2)_m Oalkyl$, $(CH_2)_m O(CH_2)_p O(CH_2)_q O(CH_2)_r CH_3$ or $CH_2$—Y—$CH_3$ where each of m, p and q is 1, 2 or 3; and r is 0, 1 or 2, Y is O or NH; and $R^2$ is H, $(CH_2)_n OH$, COOH, or $COOR^4$, where $R^4$ is $C_1$-$C_6$ alkyl or $(CH_2CH_2O)_n CH_3$, where n is 1, 2, or 3.

In one embodiment, the ibogaine derivative is represented by Formula II:

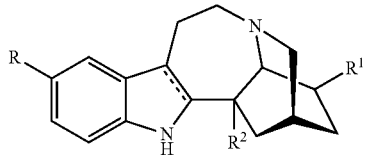

or a pharmaceutically acceptable salt and/or solvate thereof, wherein
R is $OCH_3$;
$R^1$ is $CH_2CH_3$; and
$R^2$ is $COOR^4$, where $R^4$ is $(CH_2CH_2O)_nCH_3$, where n is 1.

In another embodiment, ibogaine or a pharmaceutically acceptable salt and/or solvate thereof is utilized. In another embodiment, ibogaine or a pharmaceutically acceptable salt and/or solvate thereof is utilized. In another embodiment, the ibogaine, ibogaine derivative, is chosen from the group consisting of ibogaine, coronaridine, ibogamine, voacangine, 18-methoxycoronaridine, 2-methoxyethyl-18-methoxycoronaridinate, 18-methylaminocoronaridine or a pharmaceutically acceptable salt and/or solvate thereof.

In another embodiment, the compound utilized herein is chosen from the group consisting of ibogaine, coronaridine, ibogamine, voacangine, 18-methoxycoronaridine, 2-methoxyethyl-18-methoxycoronaridinate, 18-methylaminocoronaridine and a pharmaceutically acceptable salt and/or solvate.

In another embodiment, the compound utilized herein is selected from the group consisting of 16-hydroxymethyl-18-hydroxyibogaline, 16-hydroxymethyl-18-methoxyibogaline, 16-ethoxycarbonyl-18-hydroxyibogaline laurate, and 16-ethoxycarbonyl-18-hydroxyibogaline methoxyethoxymethyl ether and a pharmaceutically acceptable salt and/or solvate thereof.

When replacing ibogaine, the compounds of formula I, II, and subformulas thereof as utilized herein exclude ibogaine.

In a preferred embodiment, the compound utilized herein is:

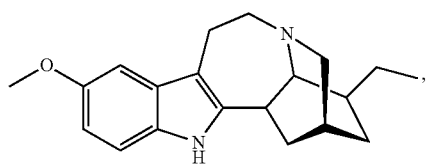

a pharmaceutically acceptable salt thereof, or a solvate of each thereof

DETAILED DESCRIPTION

It is to be understood that this invention is not limited to particular embodiments described, as such may, of course, vary. It is also to be understood that the terminology used herein is for the purpose of describing particular embodiments only, and is not intended to be limiting, since the scope of this invention will be limited only by the appended claims.

The detailed description of the invention is divided into various sections only for the reader's convenience and disclosure found in any section may be combined with that in another section. Unless defined otherwise, all technical and scientific terms used herein have the same meaning as commonly understood by one of ordinary skill in the art to which this invention belongs.

It must be noted that as used herein and in the appended claims, the singular forms "a", "an", and "the" include plural referents unless the context clearly dictates otherwise. Thus, for example, reference to "a compound" includes a plurality of compounds.

I. Definitions

Unless defined otherwise, all technical and scientific terms used herein have the same meaning as commonly understood by one of ordinary skill in the art to which this invention belongs. As used herein the following terms have the following meanings.

The term "about" when used before a numerical designation, e.g., temperature, time, amount, concentration, and such other, including a range, indicates approximations which may vary by (+) or (−) 10%, 5% or 1% % or any subrange or subvalue there between.

"Administration" refers to introducing ibogaine, an ibogaine derivative, or a pharmaceutically acceptable salt and/or solvate thereof into a patient. Typically, an effective amount is administered, which amount can be determined by the treating physician or the like. Any route of administration, such as oral, topical, subcutaneous, peritoneal, intra-arterial, inhalation, vaginal, rectal, nasal, introduction into the cerebrospinal fluid, or instillation into body compartments can be used. The ibogaine may be administered by direct blood stream delivery, e.g. sublingual, intranasal, or intrapulmonary administration.

The related terms and phrases "administering" and "administration of", when used in connection with a compound or pharmaceutical composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer a drug and/or provides a patient with a prescription for a drug is administering the drug to the patient.

"Periodic administration" or "periodically administering" refers to multiple treatments that occur on a daily, weekly, or monthly basis. Periodic administration may also refer to administration of ibogaine one, two, three, or more times per day. Administration may be via transdermal patch, gum, lozenge, sublingual tablet, intranasal, intrapulmonary, oral administration, or other administration.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, ⇒ is a single bond or a double bond.

As used herein the term "solvate" is taken to mean that a solid-form of a compound that crystallizes with one or more molecules of solvent trapped inside. A few examples of solvents that can be used to create solvates, such as pharmaceutically acceptable solvates, include, but are certainly not limited to, water, methanol, ethanol, isopropanol, butanol, C1-C6 alcohols in general (and optionally substituted), tetrahydrofuran, acetone, ethylene glycol, propylene glycol, acetic acid, formic acid, water, and solvent mixtures thereof. Other such biocompatible solvents which may aid in making a pharmaceutically acceptable solvate are well known in the art and applicable to the present invention. Additionally, various organic and inorganic acids and bases can be added or even used alone as the solvent to create a desired solvate. Such acids and bases are known in the art. When the solvent is water, the solvate can be referred to as a hydrate. Further, by being left in the atmosphere or recrystallized, the compounds of the present invention may absorb moisture, may include one or more molecules of water in the formed crystal, and thus become a hydrate. Even when such hydrates are formed, they are included in the term "solvate". Solvate also is meant to include such compositions where another compound or complex co-crystallizes with the compound of interest.

As used herein, the term "alkyl" refers to monovalent saturated aliphatic hydrocarbyl groups having from 1 to 12 carbon atoms, 1 to 10 carbon atoms, preferably 1 to 6 carbon atoms, and more preferably 1 to 3 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—). The term "$C_x$ alkyl" refers to an alkyl group having x carbon atoms, wherein x is an integer, for example, $C_3$ refers to an alkyl group having 3 carbon atoms.

"Substituted alkyl" refers to an alkyl group having from 1 to 5, preferably 1 to 3, or more preferably 1 to 2 substituents selected from the group consisting of alkoxy, $R^{20}$—C(O)—, —NR$^{20}$C(O)R$^{20}$, $R^{20}$—C(O)O—, —NR$^{20}$R$^{20}$, —C(O)NR$^{20}$R$^{20}$, —C(S)NR$^{20}$R$^{20}$, —NR$^{20}$C(O)NR$^{20}$R$^{20}$, —NR$^{20}$C(S)NR$^{20}$R$^{20}$, —O—C(O)NR$^{20}$R$^{20}$, —S(O)$_2$NR$^{20}$R$^{20}$, —O—S(O)$_2$NR$^{20}$R$^{20}$, —NR$^{20}$—S(O)$_2$NR$^{20}$R$^{20}$, —C(=NR$^{20}$)NR$^{20}$R$^{20}$, aryl, aryloxy, arylthio, azido, carboxyl, —C(O)O—R$^{21}$, —NR$^{20}$—C(O)O—R$^{21}$, —O—C(O)O—R$^{21}$, cyano, cycloalkyl, cycloalkyloxy, cycloalkylthio, —NR$^{20}$C(=NR$^{20}$)N(R$^{20}$)$_2$, halo, hydroxy, hydroxyamino, alkoxyamino, —NR$^{20}$NR$^{20}$R$^{20}$, heteroaryl, heteroaryloxy, heteroarylthio, heterocyclic, heterocyclyloxy, heterocyclylthio, nitro, spirocycloalkyl, SO$_3$H, —OS(O)$_2$—R$^{21}$, —S(O)$_2$—R$^{21}$, —C(S)—R$^{21}$, thiocyanate, thiol, and alkylthio; each R$^{20}$ is independently selected from the group consisting of hydrogen, alkyl, cycloalkyl, aryl, heteroaryl, and heterocycle, or two R$^{20}$ groups attached to a common atom are optionally joined together with the atom bound thereto to form a heterocycle; and each R$^{21}$ is independently selected from the group consisting of alkyl, cycloalkyl, aryl, heteroaryl, and heterocycle.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is at an aromatic carbon atom. Preferred aryl groups include phenyl and naphthyl.

"Substituted aryl" refers to aryl groups which are substituted with 1 to 5, preferably 1 to 3, or more preferably 1 to 2 substituents selected from the group consisting of alkyl, substituted alkyl, alkoxy, —C(O)—R$^{20}$, —NR$^{20}$C(O)R$^{20}$, $R^{20}$—C(O)O—, —NR$^{20}$R$^{20}$, —C(O)NR$^{20}$R$^{20}$, —C(S)NR$^{20}$R$^{20}$, —NR$^{20}$C(O)NR$^{20}$R$^{20}$, —NR$^{20}$C(S)NR$^{20}$R$^{20}$, —O—C(O)NR$^{20}$R$^{20}$, —S(O)$_2$NR$^{20}$R$^{20}$, —O—S(O)$_2$NR$^{20}$R$^{20}$, —NR$^{20}$—S(O)$_2$NR$^{20}$R$^{20}$, —C(=NR$^{20}$)NR$^{20}$R$^{20}$, aryl, aryloxy, arylthio, azido, carboxyl, —C(O)O—R$^{21}$, —NR$^{20}$—C(O)O—R$^{21}$, —O—C(O)O—R$^{21}$, cyano, cycloalkyl, cycloalkyloxy, cycloalkylthio, —NR$^{20}$C(=NR$^{20}$)N(R$^{20}$)$_2$, halo, hydroxy, hydroxyamino, alkoxyamino, —NR$^{20}$NR$^{20}$R$^{20}$, heteroaryl, heteroaryloxy, heteroarylthio, heterocyclic, heterocyclyloxy, heterocyclylthio, nitro, spirocycloalkyl, SO$_3$H, —OS(O)$_2$—R$^{21}$, —S(O)$_2$—R$^{21}$, —C(S)—R$^{21}$, thiocyanate, thiol, and alkylthio; each R$^{20}$ is independently selected from the group consisting of hydrogen, alkyl, cycloalkyl, aryl, heteroaryl, and heterocycle, or two R$^{20}$ groups attached to a common atom are optionally joined together with the atom bound thereto to form a heterocycle; and each R$^{21}$ is independently selected from the group consisting of alkyl, cycloalkyl, aryl, heteroaryl, and heterocycle.

"Cyano" refers to the group —CN.

"Cycloalkyl" refers to cyclic alkyl groups of from 3 to 10 or 3 to 8 carbon atoms having single or multiple cyclic rings including fused, bridged, and spiro ring systems. One or more of the rings can be aryl, heteroaryl, or heterocyclic provided that the point of attachment is through the non-aromatic, non-heterocyclic ring carbocyclic ring. Examples of suitable cycloalkyl groups include, for instance, adamantyl, cyclopropyl, cyclobutyl, cyclopentyl, and cyclooctyl. Other examples of cycloalkyl groups include bicycle[2,2,2,]octanyl, norbornyl, and spirobicyclo groups such as spiro[4.5]dec-8-yl.

"Substituted cycloalkyl" refers to a cycloalkyl group having from 1 to 5 or preferably 1 to 3 substituents selected from the group consisting of oxo, thione, alkyl, substituted alkyl, alkoxy, —C(O)—R$^{20}$, —NR$^{20}$C(O)R$^{20}$, R$^{20}$—C(O)O—, —NR$^{20}$R$^{20}$, —C(O)NR$^{20}$R$^{20}$, —C(S)NR$^{20}$R$^{20}$, —NR$^{20}$C(O)NR$^{20}$R$^{20}$, —NR$^{20}$C(S)NR$^{20}$R$^{20}$, —O—C(O)NR$^{20}$R$^{20}$, —S(O)$_2$NR$^{20}$R$^{20}$, —O—S(O)$_2$NR$^{20}$R$^{20}$, —NR$^{20}$—S(O)$_2$NR$^{20}$R$^{20}$, —C(=NR$^{20}$)NR$^{20}$R$^{20}$, aryl, aryloxy, arylthio, azido, carboxyl, —C(O)O—R$^{21}$, —NR$^{20}$—C(O)O—R$^{21}$, —O—C(O)O—R$^{21}$, cyano, cycloalkyl, cycloalkyloxy, cycloalkylthio, —NR$^{20}$C(=NR$^{20}$)N(R$^{20}$)$_2$, halo, hydroxy, hydroxyamino, alkoxyamino, —NR$^{20}$NR$^{20}$R$^{20}$, heteroaryl, heteroaryloxy, heteroarylthio, heterocyclic, heterocyclyloxy, heterocyclylthio, nitro, spirocycloalkyl, SO$_3$H, —OS(O)$_2$—R$^{21}$, —S(O)$_2$—R$^{21}$, —C(S)—R$^{21}$, thiocyanate, thiol, and alkylthio; each R$^{20}$ is independently selected from the group consisting of hydrogen, alkyl, cycloalkyl, aryl, heteroaryl, and heterocycle, or two R$^{20}$ groups attached to a common atom are optionally joined together with the atom bound thereto to form a heterocycle; and each R$^{21}$ is independently selected from the group consisting of alkyl, cycloalkyl, aryl, heteroaryl, and heterocycle.

"Halo" or "halogen" refers to fluoro, chloro, bromo and iodo and preferably is fluoro or chloro.

"Haloalkyl" refers to alkyl groups substituted with 1 to 5, 1 to 3, or 1 to 2 halo groups, wherein alkyl and halo are as defined herein.

"Heteroaryl" refers to an aromatic group of from 5 to 14 ring atoms, including from 1 to 10 carbon atoms and 1 to 4 heteroatoms selected from the group consisting of oxygen, nitrogen and sulfur. In some embodiments, heteroaryl comprises 5, 6, or 7 ring atoms, including 1 to 4 heteroatoms. Such heteroaryl groups can have a single ring (e.g., pyridyl, pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, and/or sulfonyl moieties. Preferred heteroaryls include pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heterocycle" or "heterocyclic" or "heterocycloalkyl" or "heterocyclyl" refers to a saturated or partially saturated, but not aromatic, group having from 3 to 14 ring atoms, including from 1 to 10 ring carbon atoms and from 1 to 4 ring heteroatoms selected from the group consisting of nitrogen, sulfur, or oxygen. In some embodiments, heteroaryl comprises 3, 4, 5, 6 or 7 ring atoms, including 1 to 4 heteroatoms. Heterocycle encompasses single ring or multiple condensed rings, including fused bridged and spiro ring systems. In fused ring systems, one or more the rings can be cycloalkyl, aryl, or heteroaryl provided that the point of attachment is through the non-aromatic heterocyclic ring. In one embodiment, the nitrogen and/or sulfur atom(s) of the heterocyclic group are optionally oxidized to provide for the N-oxide, sulfinyl, and/or sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Ibogaine" as a specific compound refers to the compound:

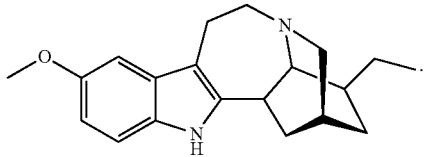

It should be understood that where "ibogaine" is mentioned herein, one more polymorphs of ibogaine can be utilized and are contemplated. Ibogaine is isolated from Tabernanth iboga, a shrub of West Africa. Ibogaine can also be synthesized using known methods. See, e.g., Büchi, et al. (1966), J. Am. Chem Society, 88(13), 3099-3109. Unless specified otherwise, "ibogaine" as used herein refers to ibogaine, ibogaine derivative, or a pharmaceutically acceptable salt and/or solvate thereof.

In some embodiments, the ibogaine is represented by Formula Ii:

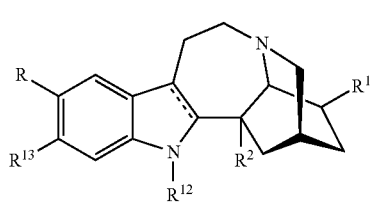

or a pharmaceutically acceptable salt and/or solvate thereof, wherein

R is H, halo, $C_1$-$C_3$ alkyl, substituted $C_1$-$C_3$ alkyl, $OR^{10}$, $NH_2$, $NHR^{10}$, $NR^{10}R^{11}$, $NHC(O)R^{10}$, or $NR^{10}C(O)R^{11}$;

$R^1$ is H, $C_1$-$C_3$ alkyl, substituted $C_1$-$C_3$ alkyl, $C_1$-$C_3$ alkoxy, $CH_2$—X—$CH_3$, or $(CH_2)_m R^3$;

$R^2$ is H, COOH, $COOR^4$, $(CH_2)_n OH$, $CH(OH)R^5$, $CH_2 OR^5$, $C(O)NH_2$, $C(O)NHR^5$, $C(O)NR^5R^6$, $C(O)NHNH_2$, $C(O)NHNHR^5$, $C(O)NHNR^5R^6$, $C(O)NR^5NH_2$, $C(O)NR^5NHR^6$, $C(O)NR^5NR^6R^7$, $C(O)NHNH(C(O)R^5)$, $C(O)NHNR^5(C(O)R^6)$, $C(O)NR^5NH(C(O)R^6)$, $C(O)NR^5NR^6(C(O)R^7)$, CN, or $C(O)R^5$;

$R^3$ is $C_1$-$C_3$ alkyl, benzyl, substituted $C_1$-$C_3$ alkyl, YH, $YR^8$, $YC(O)R^8$, $C(O)YR^8$, $C(O)NH_2$, $C(O)NHR^8$, $C(O)NR^8R^9$, $NH_2$, $NHR^8$, $NR^8R^9$, $NHC(O)R^8$, $O(CH_2)_p O(CH_2)_q O(CH_2)_r CH_3$ or $NR^8C(O)R^9$;

$R^4$ is $C_1$-$C_6$ alkyl or $(CH_2CH_2O)_n CH_3$;

$R^5$, $R^6$, $R^7$, $R^8$, $R^9$, $R^{10}$, and $R^{11}$ are independently alkyl or substituted alkyl;

$R^{12}$ is H, alkyl, or substituted alkyl;

$R^{13}$ is H, $OR^{10}$, alkyl, or substituted alkyl;

X is O or NH;

Y is O or S;

m is an integer selected from 0-8;

each of n, p and q is 1, 2 or 3; and r is 0, 1 or 2.

In some embodiments, the ibogaine is represented by Formula II:

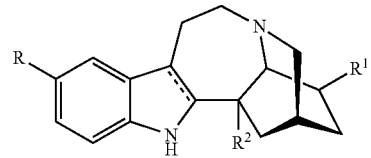

or a pharmaceutically acceptable salt and/or solvate thereof, wherein

R is hydrogen or $C_1$-$C_3$ alkoxy, $R^1$ is hydrogen, $C_1$-$C_3$ alkyl, $C_1$-$C_3$ alkoxy, $(CH_2)_m OC(O)$ alkyl, $(CH_2)_m OH$, $(CH_2)_m Oalkyl$, $(CH_2)_m O(CH_2)_p O(CH_2)_q O(CH_2)_r CH_3$ or $CH_2$—Y—$CH_3$ where each of m, p and q is 1, 2 or 3; and r is 0, 1 or 2, Y is O or NH, and $R^2$ is H, $(CH_2)_n OH$, COOH, or $COOR^4$, where $R^4$ is $C_1$-$C_6$ alkyl or $(CH_2CH_2O)_n CH_3$, where n is 1, 2, or 3.

In one embodiment, R is methoxy. In one embodiment, $R^1$ is ethyl. In one embodiment, $R^1$ is methoxy. In one embodiment, $R^1$ is $CH_2$—Y—$CH_3$ where Y is O. In one embodiment, $R^1$ is $CH_2$—Y—$CH_3$ where Y is NH. In one embodiment, $R^2$ is hydrogen. In one embodiment, In one embodiment, $R^2$ is $COOR^4$ and $R^4$ is methyl. In one embodiment, n=1. In a preferred embodiment, R, $R^1$ and $R^2$ are all not hydrogen. In one embodiment, when R is methoxy and $R^1$ is hydrogen, then $R^2$ is COOH or $COOR^4$. In another embodiment, when R is methoxy and $R^1$ is hydrogen, then X is $COOR^4$ where $R^4$ is $(CH_2CH_2O)CH_3$.

In one embodiment, $R^{12}$ is hydrogen.

In one embodiment, $R^1$ is H. In one embodiment, $R^1$ is $C_1$-$C_3$ alkyl, such as ethyl. In one embodiment, $R^1$ is $CH_2CH_2OH$. In one embodiment, $R^1$ is $CH_2CH_2OCH_3$. In one embodiment, $R^1$ is $CH_2CH_2OCH_2Ph$. In one embodiment, $R^1$ is $CH_2CH_2OC(O)alkyl$. In one embodiment, $R^1$ is $CH_2CH_2O(CH_2)_p O(CH_2)_q O(CH_2)_r CH_3$.

In one embodiment, $R^2$ is $CH_2 OH$ and $CH(OH)R^5$. In one embodiment, $R^2$ is $CH_2 OR^5$. In one embodiment, $R^2$ is $CO_2 R^5$. In one embodiment, $R^2$ is $C(O)NH_2$, $C(O)NHR^5$, or $C(O)NR^5R^6$. In one embodiment, $R^2$ is $C(O)NHNH_2$, $C(O)NHNHR^5$, $C(O)NR^5NH_2$, $C(O)NHNR^5R^6$, $C(O)NH^5NHR^6$, or $C(O)NR^5NR^6R^7$. In one embodiment, $R^2$ is $C(O)NHNH(C(O)R^5)$, $C(O)NHNR^5(C(O)R^6)$, $C(O)NR^5NH(C(O)R^6)$, or $C(O)NR^5NR^6(C(O)R^7)$. In one embodiment, $R^2$ is $C(O)R^5$.

In one embodiment, the compound is of Formula IA:

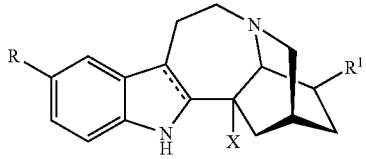

IA wherein
R is hydrogen or $C_1$-$C_3$-alkoxy,
$R^1$ is hydrogen, $C_1$-$C_3$-alkyl, $C_1$-$C_3$ alkoxy, or $CH_2$—Y—$CH_3$ where Y is O or NH, and
X is H, COOH, or $COOR^2$, where $R^2$ is $C_1$-$C_6$ alkyl or $(CH_2CH_2O)_nCH_3$, where n=1 to 3.

In another embodiment, the ibogaine derivative is represented by Formula II:

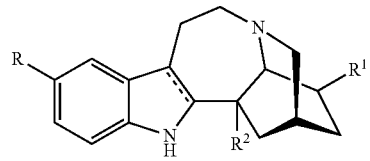

II or a pharmaceutically acceptable salt and/or solvate thereof, wherein
R is $OCH_3$;
$R^1$ is $CH_2CH_3$; and
$R^2$ is $COOR^4$, where $R^4$ is $(CH_2CH_2O)_nCH_3$, where n is 1.

When replacing ibogaine, the compounds of formula I, II, and subformulas thereof as utilized herein exclude ibogaine.

In a preferred embodiment, the compound utilized herein is:

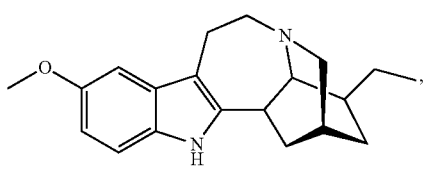

a pharmaceutically acceptable salt thereof, or a solvate of each thereof

In some embodiments, the ibogaine is selected from:

| Name | Structure |
|---|---|
| coronaridine | 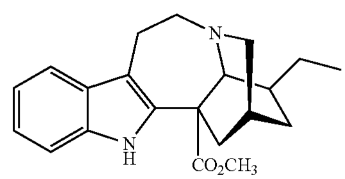 |
| 18-hydroxycoronaridine | 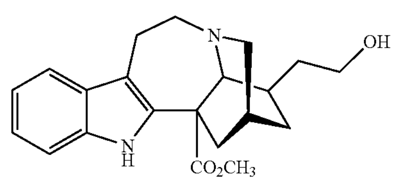 |
| 18-methoxycoronaridine | 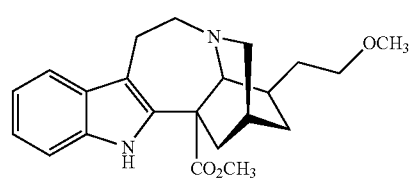 |
| 18-benzyloxycoronaridine | 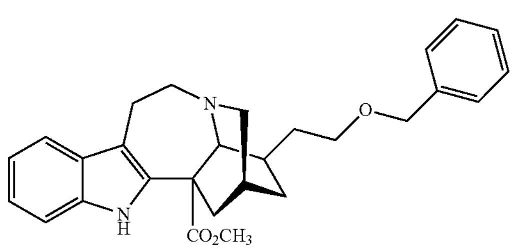 |

| Name | Structure |
|---|---|
| 18-hydroxycoronaridine laurate | 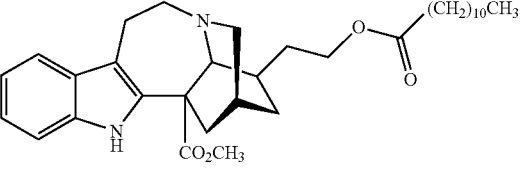 |
| 18-hydroxycoronaridine methoxyethoxymethyl ether | 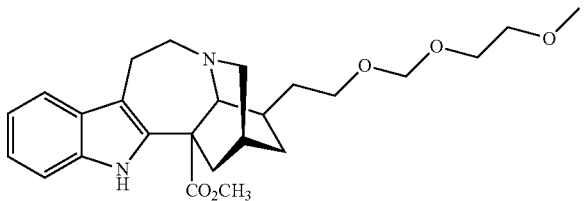 |
| 18-hydroxycoronaridine acetate | 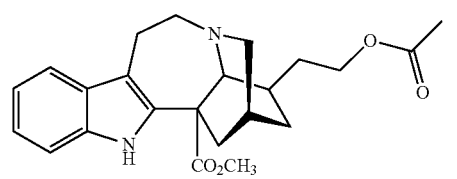 |
| voacangine | 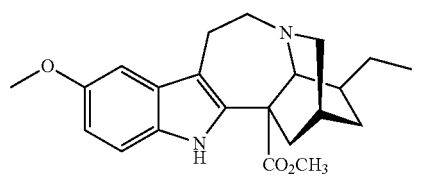 |
| 18-hydroxyvoacangine | 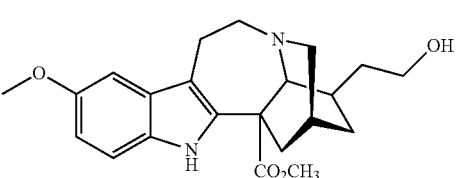 |
| 18-methoxyvoacangine | 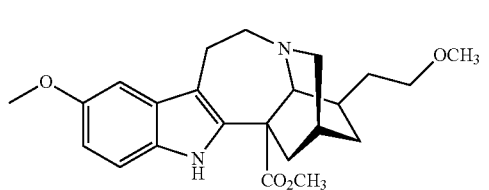 |
| 18-benzyloxyvoacangine | 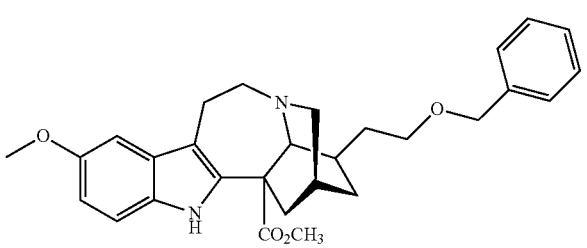 |
| 18-hydroxyvoacangine laurate | 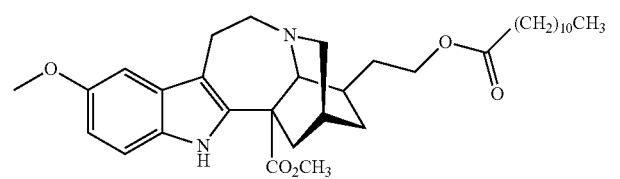 |

| Name | Structure |
|---|---|
| 18-hydroxyvoacangine acetate | 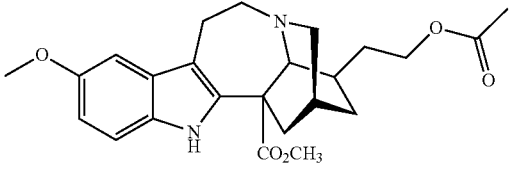 |
| 18-hydroxyvoacangine methoxyethoxymethyl ether | 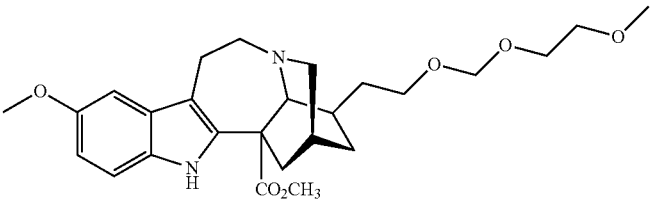 |
| conopharyngine | 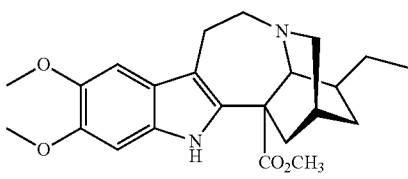 |
| 18-hydroxyconopharyngine | 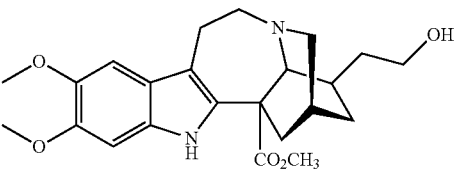 |
| 18-methoxyconopharyngine | 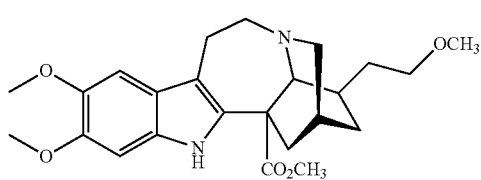 |
| 18-benzyloxyconopharyngine | 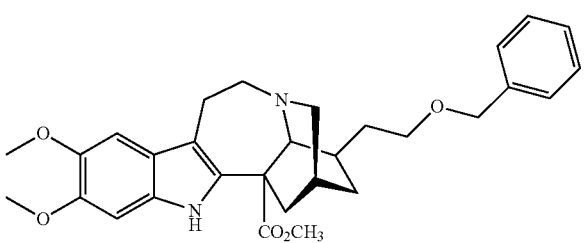 |
| 18-hydroxyconopharyngine laurate | 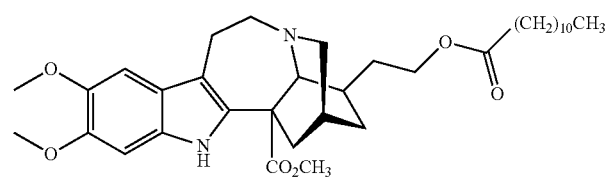 |
| 18-hydroxyconopharyngine acetate | 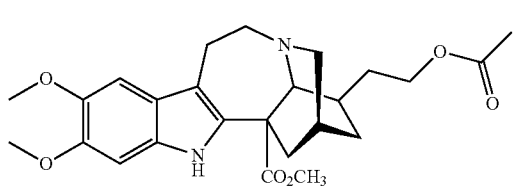 |

-continued
| Name | Structure |
|---|---|
| 18-hydroxyconopharyngine methoxyethoxymethyl ether | 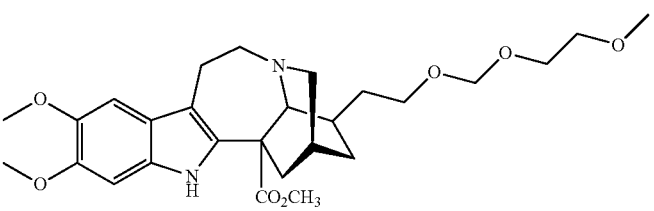 |
| ibogamine | 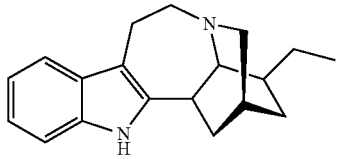 |
| 16-ethoxycarbonyl-18-hydroxyibogamine | 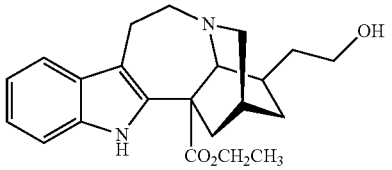 |
| 16-hydroxymethyl-18-hydroxyibogamine | 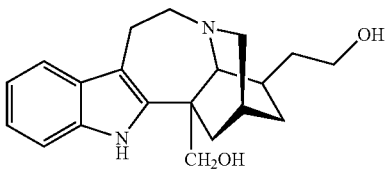 |
| 16-ethoxycarbonyl-18-methoxyibogamine | 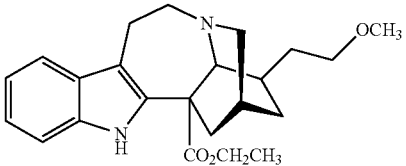 |
| 16-hydroxymethyl-18-methoxyibogamine | 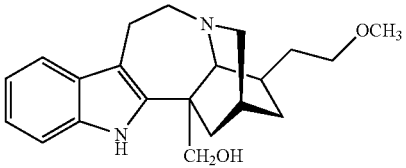 |
| 16-ethoxycarbonyl-18-benzyloxyibogamine | 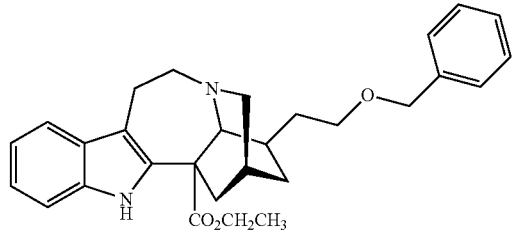 |
| 16-ethoxycarbonyl-18-hydroxyibogamine laurate | 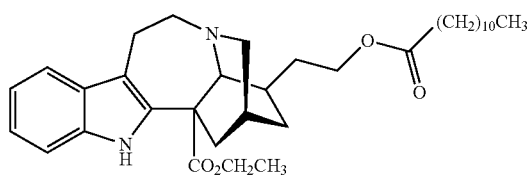 |

-continued
| Name | Structure |
|---|---|
| 16-ethoxycarbonyl-18-hydroxyibogamine acetate | 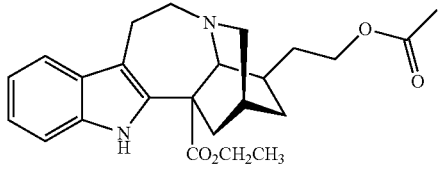 |
| 16-ethoxycarbonyl-18-hydroxyibogamine methoxyethoxymethyl ether | 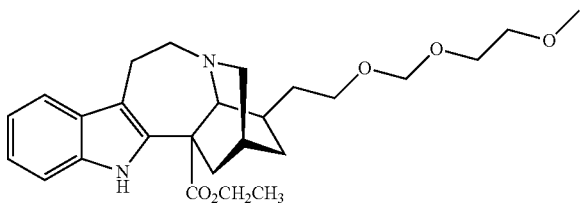 |
| ibogaine | 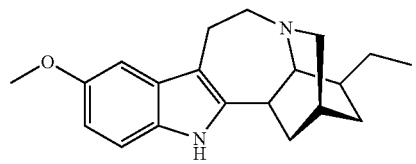 |
| 16-ethoxycarbonyl-18-hydroxyibogaine | 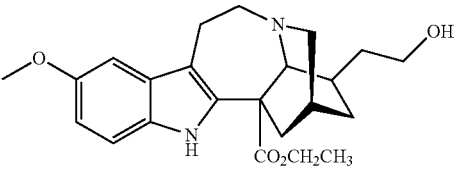 |
| 16-hydroxymethyl-18-hydroxyibogaine | 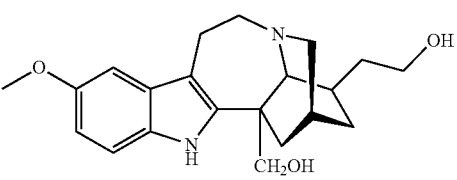 |
| 16-ethoxycarbonyl-18-methoxyibogaine | 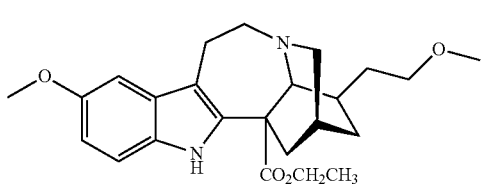 |
| 16-hydroxymethyl-18-methoxyibogaine | 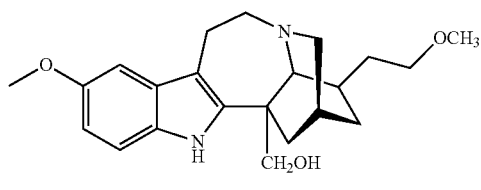 |
| 16-ethoxycarbonyl-18-benzyloxyibogaine | 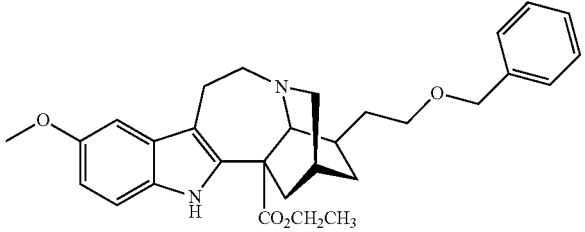 |

-continued
| Name | Structure |
|---|---|
| 16-ethoxycarbonyl-18-hydroxyibogaine laurate | 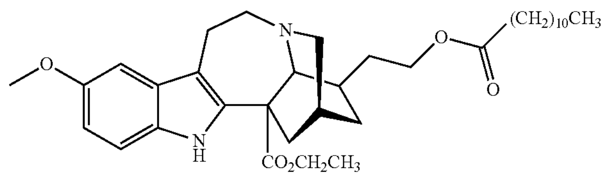 |
| 16-ethoxycarbonyl-18-hydroxyibogaine acetate | 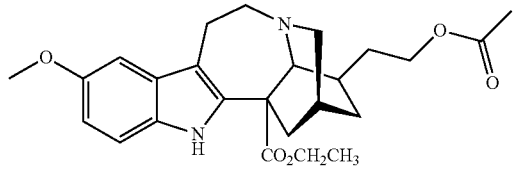 |
| 16-ethoxycarbonyl-18-hydroxyibogaine methoxyethoxymethyl ether | 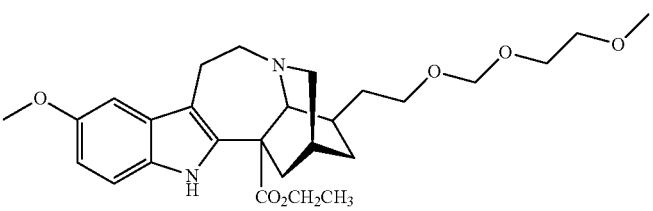 |
| ibogaline | 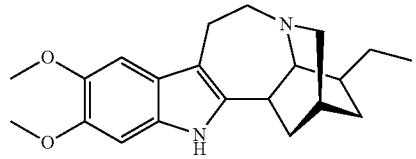 |
| 16-ethoxycarbonyl-18-hydroxyibogaline | 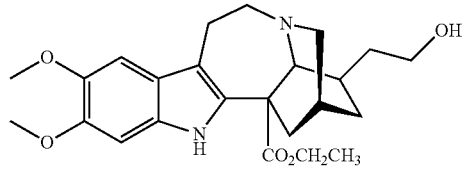 |
| 16-hydroxymethyl-18-hydroxyibogaline | 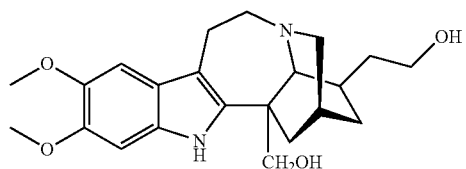 |
| 16-ethoxycarbonyl-18-methoxyibogaline | 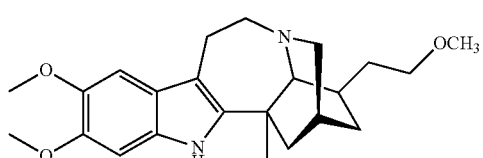 |
| 16-hydroxymethyl-18-methoxyibogaline | 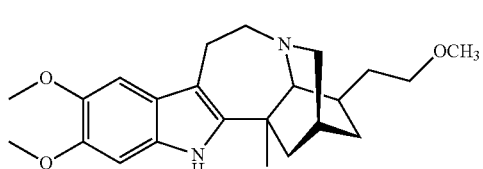 |

| Name | Structure |
|---|---|
| 16-ethoxycarbonyl-18-benzyloxyibogaline | 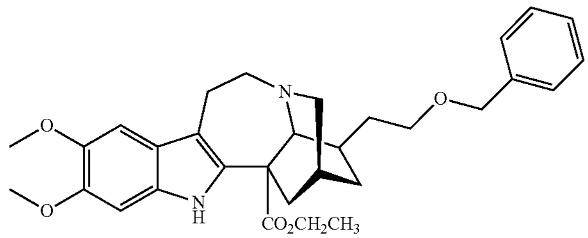 |
| 16-ethoxycarbonyl-18-hydroxyibogaline laurate | 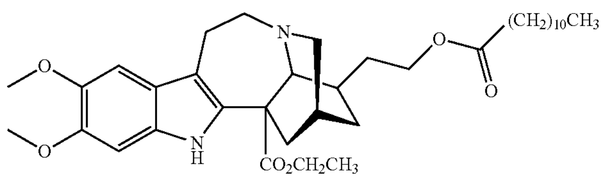 |
| 16-ethoxycarbonyl-18-hydroxyibogaline acetate | 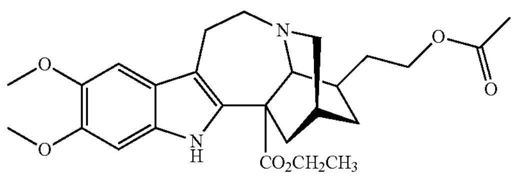 |
| 16-ethoxycarbonyl-18-hydroxyibogaline methoxyethoxymethyl ether | | and pharmaceutically acceptable salts and/or solvates thereof

In one embodiment, the ibogaine is:

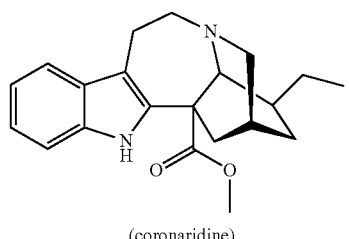

(coronaridine)

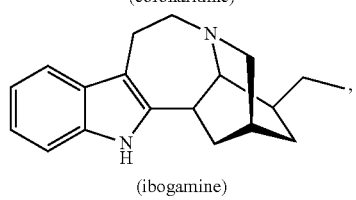

(ibogamine)

-continued

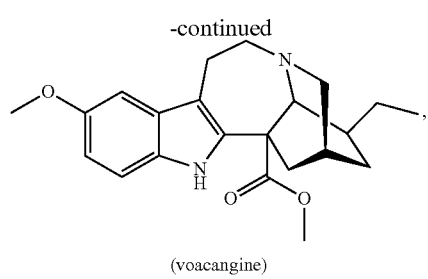

(voacangine)

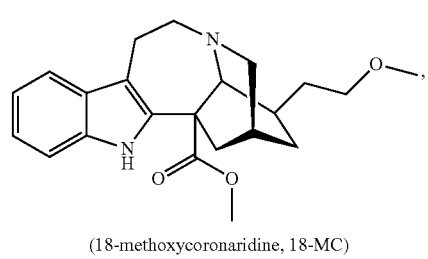

(18-methoxycoronaridine, 18-MC)

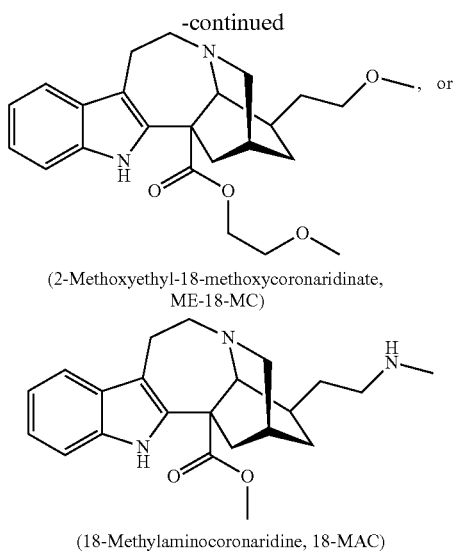

(2-Methoxyethyl-18-methoxycoronaridinate, ME-18-MC)

(18-Methylaminocoronaridine, 18-MAC)

or pharmaceutically acceptable salt and/or solvate thereof

This invention is not limited to any particular chemical form of ibogaine, an ibogaine derivative, or a pharmaceutically acceptable salt and/or solvate thereof, and the drug may be given to patients either as a free base, solvate, or as a pharmaceutically acceptable acid addition salt. In the latter case, the hydrochloride salt is generally preferred, but other salts derived from organic or inorganic acids may also be used. Examples of such acids include, without limitation, those described below as "pharmaceutically acceptable salts" and the like.

"Pharmaceutically acceptable composition" refers to a composition that is suitable for administration to a human. Such compositions include various excipients, diluents, carriers, and such other inactive agents well known to the skilled artisan.

"Pharmaceutically acceptable salt" refers to pharmaceutically acceptable salts, including pharmaceutically acceptable partial salts, of a compound, which salts are derived from a variety of organic and inorganic counter ions well known in the art and include, by way of example only, hydrochloric acid, hydrobromic acid, phosphoric acid, sulfuric acid, methane sulfonic acid, phosphorous acid, nitric acid, perchloric acid, acetic acid, tartaric acid, lactic acid, succinic acid, citric acid, malic acid, maleic acid, aconitic acid, salicylic acid, thalic acid, embonic acid, enanthic acid, oxalic acid and the like, and when the molecule contains an acidic functionality, include, by way of example only, sodium, potassium, calcium, magnesium, ammonium, tetraalkylammonium, and the like.

A "pharmaceutically acceptable solvate or hydrate" of a compound of the invention means a solvate or hydrate complex that is pharmaceutically acceptable and that possesses the desired pharmacological activity of the parent compound, and includes, but is not limited to, complexes of a compound of the invention with one or more solvent or water molecules, or 1 to about 100, or 1 to about 10, or one to about 2, 3 or 4, solvent or water molecules.

"Therapeutically effective amount" or "therapeutic amount" refers to an amount of a drug or an agent that, when administered to a patient suffering from a condition, will have the intended therapeutic effect, e.g., alleviation, amelioration, palliation or elimination of one or more manifestations of the condition in the patient. The therapeutically effective amount will vary depending upon the patient and the condition being treated, the weight and age of the subject, the severity of the condition, the salt, solvate, or derivative of the active drug portion chosen, the particular composition or excipient chosen, the dosing regimen to be followed, timing of administration, the manner of administration and the like, all of which can be determined readily by one of ordinary skill in the art. The full therapeutic effect does not necessarily occur by administration of one dose, and may occur only after administration of a series of doses. Thus, a therapeutically effective amount may be administered in one or more administrations. For example, and without limitation, a therapeutically effective amount of ibogaine, an ibogaine derivative, or a pharmaceutically acceptable salt and/or solvate thereof, in the context of treating pain, refers to an amount of ibogaine, an ibogaine derivative, or a pharmaceutically acceptable salt and/or solvate thereof that provides immediate and/or sustained pain relief for at least 2 hours beyond control (placebo), at least 5 hours beyond control, and preferably at least 10 hours beyond control.

A "therapeutic level" of a drug is an amount of ibogaine, an ibogaine derivative, or a pharmaceutically acceptable salt and/or solvate thereof that is sufficient to treat patients suffering from pain or to treat, prevent, or alleviate acute pain symptoms, but not high enough to pose any significant risk to the patient. Therapeutic levels of drugs can be determined by tests that measure the actual concentration of the compound in the blood of the patient. This concentration is referred to as the "serum concentration."

As defined herein, a "prophylactically effective amount" of a drug is an amount, typically less than the therapeutically effective amount, that provides attenuation and/or prevention of a disease or disorder or symptoms of a disease or disorder in a patient. For example, the prophylactically effective amount of the compound is expected to be less than the therapeutically effective amount because the level of inhibition does not need to be as high in a patient who is no longer physically addicted to nicotine. For example, a prophylactically effective amount is preferably 90%, 80%, 70%, 60%, 50%, 40%, 30%, 20%, or 10% less than a therapeutically effective amount. However, a prophylactically effective amount may be the same as the therapeutically effective amount, for example when a patient who is experiencing pain is administered ibogaine, an ibogaine derivative, or a pharmaceutically acceptable salt and/or solvate thereof to attenuate pain for a period of time. The prophylactically effective amount may vary for different types/categories of pain.

As defined herein, a "maintenance amount" of a drug is an amount, typically less than the therapeutically effective amount that provides attenuation and/or prevention of a disease or disorder or symptoms of a disease or disorder in a patient. The maintenance amount of the compound is expected to be less than the therapeutically effective amount because the level of inhibition does not need to be as high in a patient who is no longer manifests a disease or disorder or symptoms of a disease or disorder. For example, a maintenance amount is preferably 90%, 80%, 70%, 60%, 50%, 40%, 30%, 20%, or 10% less than a therapeutically effective amount. However, a maintenance amount may be the same as the therapeutically effective amount, for example, when a patient who is experiencing pain is administered ibogaine, an ibogaine derivative, or a pharmaceutically acceptable salt and/or solvate thereof to attenuate pain for a period of time. The maintenance amount may vary for different types/categories of pain.

"Treatment," "treating," and "treat" are defined as acting upon a disease, disorder, or condition with an agent to reduce or ameliorate harmful or any other undesired effects of the disease, disorder, or condition and/or its symptoms. "Treatment," as used herein, covers the treatment of a human patient, and includes: (a) reducing the risk of occurrence of the condition in a patient determined to be predisposed to the condition but not yet diagnosed as having the condition, (b) impeding the development of the condition, and/or (c) relieving the condition, i.e., causing regression of the condition and/or relieving one or more symptoms of the condition. "Treating" or "treatment of" a condition or patient refers to taking steps to obtain beneficial or desired results, including clinical results such as the reduction of symptoms. For purposes of this invention, beneficial or desired clinical results include, but are not limited to: pain relief in all categories and classifications of pain; treating, alleviating and/or preventing acute and/or chronic pain; treating, alleviating and/or preventing cutaneous, somatic, visceral and/or neuropathic pain; and preventing the recurrence of long-term pain.

As used herein, the term "patient" refers to mammals and includes humans and non-human mammals.

As used herein, the term "QT interval" refers to the measure of the time between the start of the Q wave and the end of the T wave in the electrical cycle of the heart. Prolongation of the QT interval refers to an increase in the QT interval.

As used herein, the term "pain" refers to all categories and classifications of pain, which are summarized below for purposes of illustration.

First, cutaneous pain is caused by injury to the skin or superficial tissues. Cutaneous nociceptors terminate just below the skin, and due to the high concentration of nerve endings, produce a well-defined, localized pain of short duration. Example injuries that produce cutaneous pain include paper cuts, minor burns (e.g., first degree burns) and superficial lacerations.

Second, somatic pain originates from ligaments, tendons, bones, blood vessels, and even nerves themselves, and is detected with somatic nociceptors. The scarcity of nociceptors in these areas produces a sharp, aching, pain of longer duration than cutaneous pain and somewhat less localized. Examples include a sprained ankle or broken bones.

Third, visceral pain originates from body organs. Visceral nociceptors are located within body organs and internal cavities. Similar to somatic pain, a scarcity of nociceptors in these areas produces a pain usually more aching and of a longer duration than somatic pain. Visceral pain may be more difficult to localize. Injuries to visceral tissue may exhibit "referred" pain, where the sensation is localized to an area completely unrelated to the site of injury. Myocardial ischaemia (i.e., the loss of blood flow to a part of the heart muscle tissue) is an example of referred pain; the sensation can occur in the upper chest as a restricted feeling, or as an ache in the left shoulder, arm, or hand. Another example of referred pain is phantom limb pain. Phantom limb pain is the sensation of pain from a limb that a person no longer has or from which the person no longer receives physical signals. This phenomena—also known as deafferentation pain—is almost universally reported by amputees and quadriplegics.

Fourth, neuropathic pain (e.g., "neuralgia") can occur as a result of injury or disease to the nerve tissue itself. The injury or disease can disrupt the ability of the sensory nerves to transmit correct information to the thalamus or cortex. Consequently, the brain interprets painful stimuli even though there is no obvious or documented physiologic cause for the pain.

Other pain classifications include acute pain and chronic pain. Acute pain is defined as short-term pain or pain with an easily identifiable cause. Acute pain indicates present damage to tissue or disease and may be "fast" and "sharp" followed by aching pain. Acute pain is centralized in one area before becoming somewhat spread out. Acute pain generally responds well to medications (e.g., morphine).

Chronic pain may be medically defined as pain that has lasted six months or longer. This constant or intermittent pain has often outlived its purpose because it does not help the body to prevent injury. It is often more difficult to treat than acute pain. Expert care is generally necessary to treat any pain that has become chronic. In addition, stronger medications are typically used for extended periods in an attempt to control the pain. This can lead to drug dependency. For example, opioids are used in some instances for prolonged periods to control chronic pain. Drug tolerance, chemical dependency, and even psychological addiction may occur.

"Nociceptive pain" refers to pain that is sensed by nociceptors, which are the nerves that sense and respond to parts of the body suffering from a damage. The nociceptors can signal tissue irritation, impending injury, or actual injury. When activated, they transmit pain signals (via the peripheral nerves as well as the spinal cord) to the brain. Nociceptive pain is typically well localized, constant, and often has an aching or throbbing quality. A subtype of nociceptive pain includes visceral pain and involves the internal organs. Visceral pain tends to be episodic and poorly localized. Nociceptive pain may be time limited; when the tissue damage heals, the pain typically resolves. However, nociceptive pain related to arthritis or cancer may not be time limited. Nociceptive pain tends to respond to treatment with opiate analgesics, such as, for example, buprenorphin, codeine, hydrocodone, oxycodone, morphine, and the like. Examples of nociceptive pain include, without limitation, pains from sprains, bone fractures, burns, bumps, bruises, inflammatory pain from an infection or arthritic disorder, pains from obstructions, cancer pain, and myofascial pain related to abnormal muscle stresses.

"Neuropathic pain" refers to chronic pain, often due to tissue injury. Neuropathic pain is generally caused by injury or damage to nerve fibers. It may include burning or coldness, "pins and needles" sensations, numbness and/or itching. It may be continuous and/or episodic. Neuropathic pain is difficult to treat, but opioids, including, without limitation, methadone, tramadol, tapentadol, oxycodone, methadone, morphine, levorphanol, and the like. Causes of neuropathic pain include, without limitation, alcoholism; amputation; back, leg, and hip problems; chemotherapy; diabetes; facial nerve problems; HIV/AIDS; multiple sclerosis; shingles; spine surgery; trigeminal neuralgia; fibromyalgia; and the like. In some cases, the cause of neuropathic pain may be unclear or unknown.

The term "dose" refers to a range of ibogaine, ibogaine derivative, or pharmaceutical salt or solvate thereof that provides a therapeutic serum level of ibogaine, an ibogaine derivative, or a pharmaceutically acceptable salt and/or solvate thereof when given to a patient in need thereof. The dose is recited in a range, for example from about 20 mg to about 120 mg, and can be expressed either as milligrams or as mg/kg body weight. The attending clinician will select an appropriate dose from the range based on the patient's weight, age, degree of addiction, health, and other relevant factors, all of which are well within the skill of the art.

The term "unit dose" refers to a dose of drug that is given to the patient to provide therapeutic results, independent of the weight of the patient. In such an instance, the unit dose is sold in a standard form (e.g., 20 mg tablet). The unit dose may be administered as a single dose or a series of subdoses. In some embodiments, the unit dose provides a standardized level of drug to the patient, independent of weight of patient. Many medications are sold based on a dose that is therapeutic to all patients based on a therapeutic window. In such cases, it is not necessary to titrate the dosage amount based on the weight of the patient.

II. Methods of the Invention

As will be apparent to the skilled artisan upon reading this disclosure, the present invention provides a method for treating pain in a patient by alleviating and/or inhibiting pain in said patient, comprising administering to the patient a dosage of ibogaine, an ibogaine derivative, or a pharmaceutically acceptable salt and/or solvate thereof.

In one aspect, this invention relates to treatment of pain in a patient suffering from pain comprising administration of a therapeutically effective amount of ibogaine, an ibogaine derivative, or a pharmaceutically acceptable salt and/or solvate thereof.

In one aspect, this invention relates to a method for treating pain in a patient suffering from pain, comprising administering to the patient a dosage of ibogaine, an ibogaine derivative, or a pharmaceutically acceptable salt and/or solvate thereof that provides an average serum concentration of about 50 ng/mL to about 850 ng/mL, said concentration being sufficient to inhibit or ameliorate said pain. In one embodiment, the dosage of ibogaine, an ibogaine derivative, or a pharmaceutically acceptable salt and/or solvate thereof results in prolongation of the QT interval of less than about 50 ms. In one embodiment, the dosage of ibogaine, an ibogaine derivative, or a pharmaceutically acceptable salt and/or solvate thereof results in a QT interval of less than about 500 ms.

In one embodiment, the average serum concentration of ibogaine, an ibogaine derivative, or a pharmaceutically acceptable salt and/or solvate thereof is from about 50 ng/mL to about 800 ng/mL or about 20 ng/mL to about 800 ng/mL. In one embodiment, the average serum concentration of ibogaine, an ibogaine derivative, or a pharmaceutically acceptable salt and/or solvate thereof is from about 50 ng/mL to about 700 ng/mL or about 20 ng/mL to about 700 ng/mL. In one embodiment, the average serum concentration of ibogaine, an ibogaine derivative, or a pharmaceutically acceptable salt and/or solvate thereof is from about 50 ng/mL to about 600 ng/mL, or about 20 ng/mL to about 600 ng/mL. In a preferred embodiment, the average serum concentration of ibogaine, an ibogaine derivative, or a pharmaceutically acceptable salt and/or solvate thereof is from about 50 ng/mL to about 500 ng/mL, or about 20 ng/mL to about 500 ng/mL. In one embodiment, the average serum concentration of ibogaine, an ibogaine derivative, or a pharmaceutically acceptable salt and/or solvate thereof or is from about 50 ng/mL to about 400 ng/mL, or about 20 ng/mL to about 400 ng/mL. In one embodiment, the average serum concentration of ibogaine, an ibogaine derivative, or a pharmaceutically acceptable salt and/or solvate thereof is from about 50 ng/mL to about 300 ng/mL, or about 20 ng/mL to about 300 ng/mL. In one embodiment, the average serum concentration of ibogaine, an ibogaine derivative, or a pharmaceutically acceptable salt and/or solvate thereof is from about 50 ng/mL to about 200 ng/mL, or about 20 ng/mL to about 200 ng/mL. In one embodiment, the average serum concentration of ibogaine, an ibogaine derivative, or a pharmaceutically acceptable salt and/or solvate thereof is from about 50 ng/mL to about 100 ng/mL, or about 20 ng/mL to about 100 ng/mL. The ranges include both extremes as well as any subranges between.

In one embodiment, the dosage or aggregate dosage of ibogaine, an ibogaine derivative, or a pharmaceutically acceptable salt and/or solvate thereof is from greater than about 1 mg/kg to about 8 mg/kg body weight per day. The aggregate dosage is the combined dosage, for example the total amount of ibogaine, an ibogaine derivative, or a pharmaceutically acceptable salt and/or solvate thereof administered over a 24-hour period where smaller amounts are administered more than once per day. In one embodiment, the therapeutically effective amount of the compound is from about 0.1 mg to about 5 mg per kg body weight per day. In another embodiment, the therapeutically effective amount of the compound is from about 0.1 mg to about 3 mg per kg body weight per day. In another embodiment, the therapeutically effective amount of the compound is from about 0.1 mg to about 2 mg per kg body weight per day. In another embodiment, the therapeutically effective amount of the compound is from about 0.1 mg to about 1.5 mg per kg body weight per day. In another embodiment, the therapeutically effective amount of the compound is from about 0.1 mg to about 1 mg per kg body weight per day. In another embodiment, the therapeutically effective amount of the compound is from about 0.5 mg to about 3 mg per kg body weight per day. In another embodiment, the therapeutically effective amount of the compound is from about 0.5 mg to about 2 mg per kg body weight per day. In another embodiment, the therapeutically effective amount of the compound is from about 0.5 mg to about 1.5 mg per kg body weight per day. In another embodiment, the therapeutically effective amount of the compound is from about 0.5 mg to about 1.3 mg per kg body weight per day. In another embodiment, the therapeutically effective amount of the compound is from about 0.5 mg to about 1.2 mg per kg body weight per day. In another embodiment, the therapeutically effective amount of the compound is from about 0.5 mg to about 1.1 mg per kg body weight per day. In another embodiment, the therapeutically effective amount of the compound is from about 0.5 mg to about 1 mg per kg body weight per day. In another embodiment, the therapeutically effective amount of the compound is from about 0.7 mg to about 1.5 mg per kg body weight per day. The ranges include both extremes as well as any subranges there between.

In one embodiment, the therapeutically effective amount of the compound is about 3 mg/kg body weight per day. In one embodiment, the therapeutically effective amount of the compound is about 2 mg/kg body weight per day. In one embodiment, the therapeutically effective amount of the compound is about 1.5 mg/kg body weight per day. In one embodiment, the therapeutically effective amount of the compound is about 1.4 mg/kg body weight per day. In one embodiment, the therapeutically effective amount of the compound is about 1.3 mg/kg body weight per day. In one embodiment, the therapeutically effective amount of the compound is about 1.2 mg/kg body weight per day. In one embodiment, the therapeutically effective amount of the compound is about 1.1 mg/kg body weight per day. In one embodiment, the therapeutically effective amount of the compound is about 1 mg/kg body weight per day. In one embodiment, the therapeutically effective amount of the compound is about 0.9 mg/kg body weight per day. In one embodiment, the therapeutically effective amount of the compound is about 0.8 mg/kg body weight per day. In one embodiment, the therapeutically effective amount of the compound is about 0.7 mg/kg body weight per day. In one embodiment, the therapeutically effective amount of the compound is about 0.6 mg/kg body weight per day. In one embodiment, the therapeutically effective amount of the compound is about 0.5 mg/kg body weight per day. In one embodiment, the therapeutically effective amount of the compound is about 0.4 mg/kg body weight per day. In one embodiment, the therapeutically effective amount of the compound is about 0.3 mg/kg body weight per day. In one embodiment, the therapeutically effective amount of the compound is about 0.2 mg/kg body weight per day. In one embodiment, the therapeutically effective amount of the compound is about 0.1 mg/kg body weight per day.

In one embodiment, the dosage or aggregate dosage of ibogaine, an ibogaine derivative, or a pharmaceutically acceptable salt and/or solvate thereof is from about 1.3 mg/kg to about 7 mg/kg body weight. In one embodiment, the dosage or aggregate dosage of ibogaine, an ibogaine derivative, or a pharmaceutically acceptable salt and/or solvate thereof is from about 1.3 mg/kg to about 6 mg/kg body weight. In one embodiment, the dosage or aggregate dosage of ibogaine, an ibogaine derivative, or a pharmaceutically acceptable salt and/or solvate thereof is from about 1.3 mg/kg to about 5 mg/kg body weight. In a preferred embodiment, the dosage or aggregate dosage of ibogaine, an ibogaine derivative, or a pharmaceutically acceptable salt and/or solvate thereof is from about 1.3 mg/kg to about 4 mg/kg body weight. In one embodiment, the dosage or aggregate dosage of ibogaine, an ibogaine derivative, or a pharmaceutically acceptable salt and/or solvate thereof is from about 1.3 mg/kg to about 3 mg/kg body weight. In one embodiment, the dosage or aggregate dosage of ibogaine, an ibogaine derivative, or a pharmaceutically acceptable salt and/or solvate thereof is from about 1.3 mg/kg to about 2 mg/kg body weight. In one embodiment, the dosage or aggregate dosage of ibogaine, an ibogaine derivative, or a pharmaceutically acceptable salt and/or solvate thereof is from about 1.5 mg/kg to about 3 mg/kg body weight. In one embodiment, the dosage or aggregate dosage of ibogaine, an ibogaine derivative, or a pharmaceutically acceptable salt and/or solvate thereof is from about 1.7 mg/kg to about 3 mg/kg body weight. In one embodiment, the dosage or aggregate dosage of ibogaine, an ibogaine derivative, or a pharmaceutically acceptable salt and/or solvate thereof is from about 2 mg/kg to about 4 mg/kg body weight. In one embodiment, the dosage or aggregate dosage of ibogaine, an ibogaine derivative, or a pharmaceutically acceptable salt and/or solvate thereof is from about 2 mg/kg to about 3 mg/kg body weight. In one embodiment, the dosage or aggregate dosage of ibogaine, an ibogaine derivative, or a pharmaceutically acceptable salt and/or solvate thereof is about 2 mg/kg body weight. The ranges include both extremes as well as any subranges there between.

In one embodiment, the dosage or aggregate dosage of ibogaine, an ibogaine derivative, or a pharmaceutically acceptable salt and/or solvate thereof is about 8 mg/kg body weight per day. In one embodiment, the dosage or aggregate dosage of ibogaine, an ibogaine derivative, or a pharmaceutically acceptable salt and/or solvate thereof is about 7 mg/kg body weight per day. In one embodiment, the dosage or aggregate dosage of ibogaine, an ibogaine derivative, or a pharmaceutically acceptable salt and/or solvate thereof is about 6 mg/kg body weight per day. In one embodiment, the dosage or aggregate dosage of ibogaine, an ibogaine derivative, or a pharmaceutically acceptable salt and/or solvate thereof is about 5 mg/kg body weight per day. In one embodiment, the dosage or aggregate dosage of ibogaine, an ibogaine derivative, or a pharmaceutically acceptable salt and/or solvate thereof is about 4 mg/kg body weight per day. In one embodiment, the dosage or aggregate dosage of ibogaine, an ibogaine derivative, or a pharmaceutically acceptable salt and/or solvate thereof is about 3 mg/kg body weight per day. In one embodiment, the dosage or aggregate dosage of ibogaine, an ibogaine derivative, or a pharmaceutically acceptable salt and/or solvate thereof is about 2 mg/kg body weight per day. In one embodiment, the dosage or aggregate dosage of ibogaine, an ibogaine derivative, or a pharmaceutically acceptable salt and/or solvate thereof is about 1.7 mg/kg body weight per day. In one embodiment, the dosage or aggregate dosage of ibogaine, an ibogaine derivative, or a pharmaceutically acceptable salt and/or solvate thereof is about 1.5 mg/kg body weight per day. In one embodiment, the dosage or aggregate dosage of ibogaine, an ibogaine derivative, or a pharmaceutically acceptable salt and/or solvate thereof is about 1.3 mg/kg body weight per day. In one embodiment, the dosage or aggregate dosage of ibogaine, an ibogaine derivative, or a pharmaceutically acceptable salt and/or solvate thereof is about 1 mg/kg body weight per day.

In one embodiment, the dosage or aggregate dosage of compound is from about 1 mg to about 4 mg per kg body weight per day. The aggregate dosage is the combined dosage, for example the total amount of ibogaine, an ibogaine derivative, or a pharmaceutically acceptable salt and/or solvate thereof administered over a 24-hour period where smaller amounts are administered more than once per day.

In one embodiment, the dosage or aggregate dosage of ibogaine, an ibogaine derivative, or a pharmaceutically acceptable salt and/or solvate thereof is between about 70 mg and about 150 mg. In one embodiment, the dosage or aggregate dosage of ibogaine, an ibogaine derivative, or a pharmaceutically acceptable salt and/or solvate thereof is between about 75 mg and about 150 mg. In one embodiment, the dosage or aggregate dosage of ibogaine, an ibogaine derivative, or a pharmaceutically acceptable salt and/or solvate thereof is between about 80 mg and about 140 mg. In one embodiment, the dosage or aggregate dosage of ibogaine, an ibogaine derivative, or a pharmaceutically acceptable salt and/or solvate thereof is between about 90 mg and about 140 mg. In one embodiment, the dosage or aggregate dosage of ibogaine, an ibogaine derivative, or a pharmaceutically acceptable salt and/or solvate thereof is between about 90 mg and about 130 mg. In one embodiment, the dosage or aggregate dosage of ibogaine, an ibogaine derivative, or a pharmaceutically acceptable salt and/or solvate thereof is between about 100 mg and about 130 mg. In one embodiment, the dosage or aggregate dosage of ibogaine, an ibogaine derivative, or a pharmaceutically acceptable salt and/or solvate thereof is between about 110 mg and about 130 mg. The ranges include both extremes as well as any subrange or subvalue there between.

In one embodiment, the average serum concentration of ibogaine, an ibogaine derivative, or a pharmaceutically acceptable salt and/or solvate thereof is from about 50 ng/mL to about 800 ng/mL or about 60 ng/mL to about 800 ng/mL. In one embodiment, the average serum concentration of ibogaine, an ibogaine derivative, or a pharmaceutically acceptable salt and/or solvate thereof is from about 50 ng/mL to about 700 ng/mL or about 60 ng/mL to about 700 ng/mL. In one embodiment, the average serum concentration of ibogaine, an ibogaine derivative, or a pharmaceutically acceptable salt and/or solvate thereof is from about 50 ng/mL to about 600 ng/mL, or about 60 ng/mL to about 600 ng/mL. In a preferred embodiment, the average serum concentration of ibogaine, an ibogaine derivative, or a pharmaceutically acceptable salt and/or solvate thereof is from about 50 ng/mL to about 500 ng/mL, or about 60 ng/mL to about 500 ng/mL. In one embodiment, the average serum concentration of ibogaine, an ibogaine derivative, or a pharmaceutically acceptable salt and/or solvate thereof is from about 50 ng/mL to about 400 ng/mL, or about 60 ng/mL to about 400 ng/mL. In one embodiment, the average serum concentration of ibogaine, an ibogaine derivative, or a pharmaceutically acceptable salt and/or solvate thereof is from about 50 ng/mL to about 300 ng/mL, or about 60 ng/mL to about 300 ng/mL. In one embodiment, the average serum concentration of ibogaine, an ibogaine derivative, or a pharmaceutically acceptable salt and/or solvate thereof is from about 50 ng/mL to about 200 ng/mL, or about 60 ng/mL to about 200 ng/mL. In one embodiment, the average serum concentration of ibogaine, an ibogaine derivative, or a pharmaceutically acceptable salt and/or solvate thereof is from about 50 ng/mL to about 100 ng/mL, or about 60 ng/mL to about 100 ng/mL. The ranges include both extremes as well as any subranges between.

In one embodiment, the average serum concentration of ibogaine, an ibogaine derivative, or a pharmaceutically acceptable salt and/or solvate thereof is from about 50 ng/mL to about 180 ng/mL, or about 60 ng/mL to about 180 ng/mL. In one embodiment, the average serum concentration of ibogaine, an ibogaine derivative, or a pharmaceutically acceptable salt and/or solvate thereof is from about 50 ng/mL to about 150 ng/mL, or about 60 ng/mL to about 150 ng/mL. In one embodiment, the average serum concentration of ibogaine, an ibogaine derivative, or a pharmaceutically acceptable salt and/or solvate thereof is from about 50 ng/mL to about 100 ng/mL, or about 60 ng/mL to about 100 ng/mL. In one embodiment, the average serum concentration of ibogaine, an ibogaine derivative, or a pharmaceutically acceptable salt and/or solvate thereof is from about 80 ng/mL to about 150 ng/mL. In one embodiment, the average serum concentration of ibogaine, an ibogaine derivative, or a pharmaceutically acceptable salt and/or solvate thereof is from about 80 ng/mL to about 100 ng/mL. In one embodiment, such a dosing regimen provides an average serum concentration of ibogaine, an ibogaine derivative, or a pharmaceutically acceptable salt and/or solvate thereof of about 50 ng/mL to about 180 ng/mL. In one embodiment, the one or more additional doses maintain an average serum concentration of about 50 ng/mL to about 180 ng/mL over a period of time. The ranges include both extremes as well as any subrange or subvalue there between.

In one embodiment, the dosage of ibogaine, an ibogaine derivative, or a pharmaceutically acceptable salt and/or solvate thereof provides a serum concentration of between about 1000 ng*hr/mL and about 6000 ng*hr/mL. In one embodiment, the dosage of ibogaine, an ibogaine derivative, or a pharmaceutically acceptable salt and/or solvate thereof provides a serum concentration of between about 1200 ng*hr/mL and about 5800 ng*hr/mL. In one embodiment, the dosage of ibogaine, an ibogaine derivative, or a pharmaceutically acceptable salt and/or solvate thereof provides a serum concentration of between about 1200 ng*hr/mL and about 5500 ng*hr/mL. The ranges include both extremes as well as any subrange or subvalue there between.

In one embodiment, the dosage of ibogaine, an ibogaine derivative, or a pharmaceutically acceptable salt and/or solvate thereof provides a maximum serum concentration (Cmax) of less than about 250 ng/mL. In one embodiment, the dosage of ibogaine, an ibogaine derivative, or a pharmaceutically acceptable salt and/or solvate thereof provides a Cmax between about 40 ng/mL and about 250 ng/mL. In a preferred embodiment, the dosage of ibogaine, an ibogaine derivative, or a pharmaceutically acceptable salt and/or solvate thereof provides a Cmax between about 60 ng/mL and about 200 ng/mL. In one embodiment, the dosage of ibogaine, an ibogaine derivative, or a pharmaceutically acceptable salt and/or solvate thereof provides a Cmax between about 100 ng/mL and about 180 ng/mL. The ranges include both extremes as well as any subrange or subvalue there between.

In another embodiment, there is provided a unit dose of ibogaine, an ibogaine derivative, or a pharmaceutically acceptable salt and/or solvate thereof which is about 50 mg to about 200 mg per dose. In one embodiment, the unit dose is about 50 to about 120 mg per dose. In one embodiment, the unit dose is about 120 mg per dose. It being understood that the term "unit dose" means a dose sufficient to provide therapeutic results whether given all at once or serially over a period of time.

In some embodiments, the patient is administered an initial dose of ibogaine, an ibogaine derivative, or a pharmaceutically acceptable salt and/or solvate thereof followed by one or more additional doses.

In some embodiments, the initial dose of ibogaine, an ibogaine derivative, or a pharmaceutically acceptable salt and/or solvate thereof is from about 75 mg to about 120 mg. In one embodiment, the initial dose is about 75 mg. In one embodiment, the initial dose is about 80 mg. In one embodiment, the initial dose is about 85 mg. In one embodiment, the initial dose is about 90 mg. In one embodiment, the initial dose is about 95 mg. In one embodiment, the initial dose is about 100 mg. In one embodiment, the initial dose is about 105 mg. In one embodiment, the initial dose is about 110 mg. In one embodiment, the initial dose is about 115 mg. In one embodiment, the initial dose is about 120 mg.

In some embodiments, the one or more additional doses are lower than the initial dose. In one embodiment, the one or more additional doses are from about 5 mg to about 50 mg. In one embodiment, the one or more additional doses may or may not comprise the same amount of ibogaine, an ibogaine derivative, or a pharmaceutically acceptable salt and/or solvate thereof. In one embodiment, at least one additional dose is about 5 mg. In one embodiment, at least one additional dose is about 10 mg. In one embodiment, at least one additional dose is about 15 mg. In one embodiment, at least one additional dose is about 20 mg. In one embodiment, at least one additional dose is about 25 mg. In one embodiment, at least one additional dose is about 30 mg. In one embodiment, at least one additional dose is about 35 mg. In one embodiment, at least one additional dose is about 40 mg. In one embodiment, at least one additional dose is about 45 mg. In one embodiment, at least one additional dose is about 50 mg.

In one embodiment, the one or more additional doses are administered periodically. In one embodiment, the one or more additional doses are administered approximately every 4 hours. In one embodiment, the one or more additional doses are administered every 6 hours. In one embodiment, the one or more additional doses are administered approximately every 8 hours. In one embodiment, the one or more additional doses are administered approximately every 10 hours. In one embodiment, the one or more additional doses are administered approximately every 12 hours. In one embodiment, the one or more additional doses are administered approximately every 18 hours. In one embodiment, the one or more additional doses are administered approximately every 24 hours. In one embodiment, the one or more additional doses are administered approximately every 36 hours. In one embodiment, the one or more additional doses are administered approximately every 48 hours.

In some embodiments, the patient is administered a high (therapeutic) dose of ibogaine, an ibogaine derivative, or a pharmaceutically acceptable salt and/or solvate thereof for a period of time to ameliorate the most significant symptoms of a disease or disorder, and then is administered a lower (maintenance) dose to prevent relapse. In some embodiments, the patient is administered a therapeutic dose of ibogaine, an ibogaine derivative, or a pharmaceutically acceptable salt and/or solvate thereof for a period of time to ameliorate the most significant symptoms, and then is administered a decreasing (tapered) amount of ibogaine, an ibogaine derivative, or a pharmaceutically acceptable salt and/or solvate thereof over time until the maintenance dose is reached.

In one embodiment, ibogaine is administered at an amount by weight that is twice that administered for noribogaine for treating a same or similar condition. For example, and without limitation, an administration of a dose 80 mg ibogaine approximates a dose of 40 mg noribogaine.

Maintenance Dose

In some embodiments, the maintenance dose of ibogaine, an ibogaine derivative, or a pharmaceutically acceptable salt and/or solvate thereof is about 10% to about 80% of the therapeutic dose. In some embodiments, the maintenance dose of ibogaine, an ibogaine derivative, or a pharmaceutically acceptable salt and/or solvate thereof is about 70% of the therapeutic dose. In some embodiments, the maintenance dose is about 60% of the therapeutic dose. In some embodiments, the maintenance dose is about 50% of the therapeutic dose. In some embodiments, the maintenance dose is about 40% of the therapeutic dose. In some embodiments, the maintenance dose is about 30% of the therapeutic dose. In some embodiments, the maintenance dose is about 20% of the therapeutic dose. In some embodiments, the maintenance dose is about 10% of the therapeutic dose.

In some embodiments, the maintenance average serum level of ibogaine, an ibogaine derivative, or a pharmaceutically acceptable salt and/or solvate thereof is about 10% to about 80% of the therapeutic average serum level of ibogaine, an ibogaine derivative, or a pharmaceutically acceptable salt and/or solvate thereof. In some embodiments, the maintenance average serum level of ibogaine, an ibogaine derivative, or a pharmaceutically acceptable salt and/or solvate thereof is about 70% of the therapeutic average serum level of ibogaine, an ibogaine derivative, or a pharmaceutically acceptable salt and/or solvate thereof. In some embodiments, the maintenance average serum level of ibogaine, an ibogaine derivative, or a pharmaceutically acceptable salt and/or solvate thereof is about 60% of the therapeutic average serum level of ibogaine, an ibogaine derivative, or a pharmaceutically acceptable salt and/or solvate thereof. In some embodiments, the maintenance average serum level of ibogaine, an ibogaine derivative, or a pharmaceutically acceptable salt and/or solvate thereof is about 50% of the therapeutic average serum level of ibogaine, an ibogaine derivative, or a pharmaceutically acceptable salt and/or solvate thereof. In some embodiments, the maintenance average serum level of ibogaine, an ibogaine derivative, or a pharmaceutically acceptable salt and/or solvate thereof is about 40% of the therapeutic average serum level of ibogaine, an ibogaine derivative, or a pharmaceutically acceptable salt and/or solvate thereof. In some embodiments, the maintenance average serum level of ibogaine, an ibogaine derivative, or a pharmaceutically acceptable salt and/or solvate thereof is about 30% of the therapeutic average serum level of ibogaine, an ibogaine derivative, or a pharmaceutically acceptable salt and/or solvate thereof. In some embodiments, the maintenance average serum level of ibogaine, an ibogaine derivative, or a pharmaceutically acceptable salt and/or solvate thereof is about 20% of the therapeutic average serum level of ibogaine, an ibogaine derivative, or a pharmaceutically acceptable salt and/or solvate thereof. In some embodiments, the maintenance average serum level of ibogaine, an ibogaine derivative, or a pharmaceutically acceptable salt and/or solvate thereof is about 10% of the therapeutic average serum level of ibogaine, an ibogaine derivative, or a pharmaceutically acceptable salt and/or solvate thereof.

Tapered Dosing

In some embodiments, the therapeutic dose of ibogaine, an ibogaine derivative, or a pharmaceutically acceptable salt and/or solvate thereof is a tapered dosing over a period of time, during which the patient is detoxified, for example, without suffering significant acute withdrawal symptoms. Without being bound by theory, it is believed that tapering will allow the full therapeutic effect of ibogaine, an ibogaine derivative, or a pharmaceutically acceptable salt and/or solvate thereof with less prolongation of the QT interval. Tapering involves administration of one or more subsequently lower doses of ibogaine, an ibogaine derivative, or a pharmaceutically acceptable salt and/or solvate thereof over time. For example, in some embodiments, the first tapered dose is about 50% to about 95% of the first or original dose. In some embodiments, the second tapered dose is about 40% to about 90% of the first or original dose. In some embodiments, the third tapered dose is about 30% to about 85% of the first or original dose. In some embodiments, the fourth tapered dose is about 20% to about 80% of the first or original dose. In some embodiments, the fifth tapered dose is about 10% to about 75% of the first or original dose.

In some embodiments, the first tapered dose is given after the first dose of ibogaine, an ibogaine derivative, or a pharmaceutically acceptable salt and/or solvate thereof. In some embodiments, the first tapered dose is given after the second, third, or a subsequent dose of compound. The first tapered dose may be administered at any time after the previous dose of compound.

In one embodiment, the therapeutic dose of ibogaine, an ibogaine derivative, or a pharmaceutically acceptable salt and/or solvate thereof is tapered over time until the desired maintenance dose is reached. For example, in some embodiments, the first tapered dose is about 50% to about 95% of the therapeutic dose. In some embodiments, the second tapered dose is about 40% to about 90% of the therapeutic dose. In some embodiments, the third tapered dose is about 30% to about 85% of the therapeutic dose. In some embodiments, the fourth tapered dose is about 20% to about 80% of the therapeutic dose. In some embodiments, the fifth tapered dose is about 10% to about 75% of the therapeutic dose. In some embodiments, one tapered dose is given to achieve the maintenance dose. In some embodiments, two tapered doses are given to achieve the maintenance dose. In some embodiments, three tapered doses are given to achieve the maintenance dose. In some embodiments, four or more tapered doses are given to achieve the maintenance dose. Determination of the tapered doses, number of tapered doses, and the like can be readily made a qualified clinician.

The first tapered dose may be administered at any time after the previous dose of ibogaine, an ibogaine derivative, or a pharmaceutically acceptable salt and/or solvate thereof. The first tapered dose can be given once, for example, followed by subsequent further tapered doses, or it can be given multiple times with or without subsequent, further tapered doses (e.g., second, third, fourth, etc. tapered doses), which likewise can be given once or over multiple administrations, for example. In some embodiments, the first tapered dose is given after the first dose of ibogaine, an ibogaine derivative, or a pharmaceutically acceptable salt and/or solvate thereof. In some embodiments, the first tapered dose is given after the second, third, or a subsequent dose of ibogaine, an ibogaine derivative, or a pharmaceutically acceptable salt and/or solvate thereof. In some embodiments, the first tapered dose is administered one hour, 6 hours, 12 hours, 18 hours, 24 hours, 36 hours, 48 hours, or more after the previous dose of ibogaine, an ibogaine derivative, or a pharmaceutically acceptable salt and/or solvate thereof. Similarly, second, third, fourth, etc. tapered doses, if given, can be given one hour, 6 hours, 12 hours, 18 hours, 24 hours, 36 hours, 48 hours, or more after the previous dose of ibogaine, an ibogaine derivative, or a pharmaceutically acceptable salt and/or solvate thereof.

In some embodiments, one tapered dose is given to achieve the desired lower therapeutic dose. In some embodiments, two tapered doses are given to achieve the desired lower therapeutic dose. In some embodiments, three tapered doses are given to achieve the desired lower therapeutic dose. In some embodiments, four or more tapered doses are given to achieve the desired lower therapeutic dose. Determination of the tapered doses, number of tapered doses, and the like can be readily made a qualified clinician.

In some embodiments, the patient undergoes long-term (e.g., one month, three months, six months, one year or longer) treatment with maintenance doses of ibogaine, an ibogaine derivative, or a pharmaceutically acceptable salt and/or solvate thereof. In some embodiments, the patient is treated for acute withdrawal with therapeutic doses of ibogaine, an ibogaine derivative, or a pharmaceutically acceptable salt and/or solvate thereof as described above, and then the amount of ibogaine, an ibogaine derivative, or a pharmaceutically acceptable salt and/or solvate thereof is reduced to maintenance levels after acute withdrawal symptoms would be expected to have subsided. Acute withdrawal symptoms generally are the most pronounced in the first week after cessation of alcohol use, although acute withdrawal may last as long as six weeks or more.

In one embodiment, the QT interval is not prolonged more than about 50 ms. In one embodiment, the QT interval is not prolonged more than about 40 ms. In one embodiment, the QT interval is not prolonged more than about 30 ms. In one embodiment, the QT interval is not prolonged more than about 20 ms. In one embodiment, the QT interval is not prolonged more than about 10 ms.

In some embodiments, the patient is administered periodically, such as once, twice, three time, four times or five times daily with ibogaine, an ibogaine derivative, or a pharmaceutically acceptable salt and/or solvate thereof. In some embodiments, the administration is once daily, or once every second day, once every third day, three times a week, twice a week, or once a week. The dosage and frequency of the administration depends on the route of administration, dosage, age and body weight of the patient, condition of the patient, without limitation. Determination of dosage and frequency suitable for the present technology can be readily made a qualified clinician.

In one embodiment, the QT interval is not prolonged more than about 50 ms. In one embodiment, the QT interval is not prolonged more than about 40 ms. In one embodiment, the QT interval is not prolonged more than about 30 ms. In one embodiment, the QT interval is not prolonged more than about 20 ms. In one embodiment, the QT interval is not prolonged more than about 10 ms.

Ibogaine suitable for administration in accordance with the methods provide herein, can be suitable for a variety of delivery modes including, without limitation, oral and transdermal delivery. Compositions suitable for internal, pulmonary, rectal, nasal, vaginal, lingual, intravenous, intra-arterial, intramuscular, intraperitoneal, intracutaneous and subcutaneous routes may also be used. Possible dosage forms include tablets, capsules, pills, powders, aerosols, suppositories, parenterals, and oral liquids, including suspensions, solutions and emulsions. Sustained release dosage forms may also be used. All dosage forms may be prepared using methods that are standard in the art (see e.g., Remington's Pharmaceutical Sciences, 16th ed., A. Oslo editor, Easton Pa. 1980).

Ibogaine, an ibogaine derivative, or a pharmaceutically acceptable salt and/or solvate thereof can also be used in conjunction with any of the vehicles and excipients commonly employed in pharmaceutical preparations, e.g., talc, gum Arabic, lactose, starch, magnesium stearate, cocoa butter, aqueous or non-aqueous solvents, oils, paraffin derivatives, glycols, etc. Coloring and flavoring agents may also be added to preparations, particularly to those for oral administration. Solutions can be prepared using water or physiologically compatible organic solvents such as ethanol, 1,2-propylene glycol, polyglycols, dimethylsulfoxide, fatty alcohols, triglycerides, partial esters of glycerine and the like. Parenteral compositions containing ibogaine may be prepared using conventional techniques that may include sterile isotonic saline, water, 1,3-butanediol, ethanol, 1,2-propylene glycol, polyglycols mixed with water, Ringer's solution, etc.

The compositions utilized herein may be formulated for aerosol administration, particularly to the respiratory tract and including intrapulmonary or intranasal administration. The compound will generally have a small particle size, for example of the order of 5 microns or less. Such a particle size may be obtained by means known in the art, for example by micronization. The active ingredient may be provided in a pressurized pack with a suitable propellant such as a chlorofluorocarbon (CFC), (for example, dichlorodifluoromethane, trichlorofluoromethane, or dichlorotetrafluoroethane), carbon dioxide or other suitable gases. The aerosol may conveniently also contain a surfactant such as lecithin. The dose of drug may be controlled by a metered valve. Alternatively, the active ingredients may be provided in the form of a dry powder, for example a powder mix of the compound in a suitable powder base such as lactose, starch, starch derivatives such as hydroxypropylmethyl cellulose and polyvinylpyrrolidine. In some embodiments, the powder carrier will form a gel in the nasal cavity. The powder composition may be presented in unit dose form, for example in capsules or cartridges, gelatin or blister packs, from which the powder may be administered by means of an inhaler.

In some embodiments, ibogaine, an ibogaine derivative, or a pharmaceutically acceptable salt and/or solvate thereof is administered orally, which may conveniently be provided in tablet, caplet, sublingual, liquid or capsule form. In certain embodiments, the ibogaine, an ibogaine derivative, or a pharmaceutically acceptable salt and/or solvate thereof is provided as ibogaine HCl, with dosages reported as the amount of free base ibogaine. In some embodiments, the ibogaine HCl is provided in hard gelatin capsules containing only ibogaine HCl with no excipients.

The compositions utilized herein may be formulated for sublingual administration, for example as sublingual tablets. Sublingual tablets are designed to dissolve very rapidly. The formulations of these tablets contain, in addition to the drug, a limited number of soluble excipients, usually lactose and powdered sucrose, but sometimes dextrose and mannitol.

It has been discovered that ibogaine has a bitter taste to at least some patients. Accordingly, compositions for oral use (including sublingual, inhaled, and other oral formulations) may be formulated to utilize taste-masking technologies. A number of ways to mask the taste of bitter drugs are known in the art, including addition of sugars, flavors, sweeteners, or coatings; use of lipoproteins, vesicles, and/or liposomes; granulation; microencapsulation; numbing of taste buds; multiple emulsion; modification of viscosity; or salt formation; inclusion or molecular complexes; ion exchange resins; and solid dispersion. Any method of masking the bitterness of the compound of the invention may be used.

Patient Pre-Screening and Monitoring

Pre-screening of patients before treatment with ibogaine, an ibogaine derivative, or a pharmaceutically acceptable salt and/or solvate thereof and/or monitoring of patients during ibogaine, an ibogaine derivative, or a pharmaceutically acceptable salt and/or solvate thereof treatment may be required to ensure that QT interval is not prolonged beyond a certain value. For example, QT interval greater than 500 ms can be considered dangerous for individual patients. Pre-screening and/or monitoring may be necessary at high levels of ibogaine, an ibogaine derivative, or a pharmaceutically acceptable salt and/or solvate thereof treatment. Pre-screening of patients may not be necessary at lower doses of ibogaine, an ibogaine derivative, or a pharmaceutically acceptable salt and/or solvate thereof treatment.

In one embodiment, a patient receiving a therapeutic dose of ibogaine, an ibogaine derivative, or a pharmaceutically acceptable salt and/or solvate thereof is monitored in a clinical setting. Monitoring may be necessary to ensure the QT interval is not prolonged to an unacceptable degree. A "clinical setting" refers to an inpatient setting (e.g., inpatient clinic, hospital, rehabilitation facility) or an outpatient setting with frequent, regular monitoring (e.g., outpatient clinic that is visited daily to receive dose and monitoring). Monitoring includes monitoring of QT interval. Methods for monitoring of QT interval are well-known in the art, for example by ECG.

In one embodiment, a patient receiving a therapeutic dose of ibogaine, an ibogaine derivative, or a pharmaceutically acceptable salt and/or solvate thereof is not monitored in a clinical setting. In one embodiment, a patient receiving ibogaine, an ibogaine derivative, or a pharmaceutically acceptable salt and/or solvate thereof treatment is monitored periodically, for example daily, weekly, monthly, or occasionally. In one embodiment, the patient is not monitored.

In one aspect, this invention relates to a method for treating or attenuating pain and/or symptoms of pain in a patient, comprising selecting a patient suffering from pain who is prescreened to evaluate the patient's expected tolerance for prolongation of QT interval, administering to the patient a dosage of ibogaine, an ibogaine derivative, or a pharmaceutically acceptable salt and/or solvate thereof that provides an average serum concentration of about 50 ng/mL to about 850 ng/mL, said concentration being sufficient to treat pain and/or symptoms of pain while maintaining a QT interval of less than 500 ms during said treatment. In some embodiments, the concentration is sufficient to treat pain and/or symptoms of pain while maintaining a QT interval of less than about 470 ms during treatment. Preferably, the concentration is sufficient to treat pain and/or symptoms of pain while maintaining a QT interval of less than about 450 ms during treatment. In one embodiment, the concentration is sufficient to treat pain and/or symptoms of pain while maintaining a QT interval of less than about 420 ms during treatment.

In one embodiment, prescreening of the patient comprises ascertaining that ibogaine, an ibogaine derivative, or a pharmaceutically acceptable salt and/or solvate thereof treatment will not result in a QT interval over about 500 ms. In one embodiment, prescreening of the patient comprises ascertaining that ibogaine, an ibogaine derivative, or a pharmaceutically acceptable salt and/or solvate thereof treatment will not result in a QT interval over about 470 ms. In one embodiment, prescreening comprises ascertaining that ibogaine, an ibogaine derivative, or a pharmaceutically acceptable salt and/or solvate thereof treatment will not result in a QT interval over about 450 ms. In one embodiment, prescreening comprises ascertaining that ibogaine, an ibogaine derivative, or a pharmaceutically acceptable salt and/or solvate thereof treatment will not result in a QT interval over about 420 ms. In one embodiment, prescreening comprises determining the patient's pre-treatment QT interval.

As it relates to pre-screening or pre-selection of patients, patients may be selected based on any criteria as determined by the skilled clinician. Such criteria may include, by way of non-limiting example, pre-treatment QT interval, pre-existing cardiac conditions, risk of cardiac conditions, age, sex, general health, and the like. The following are examples of selection criteria for disallowing ibogaine, an ibogaine derivative, or a pharmaceutically acceptable salt and/or solvate thereof treatment or restricting dose of ibogaine, an ibogaine derivative, or a pharmaceutically acceptable salt and/or solvate thereof administered to the patient: high QT interval before treatment (e.g., such that there is a risk of the patient's QT interval exceeding 500 ms during treatment); congenital long QT syndrome; bradycardia; hypokalemia or hypomagnesemia; recent acute myocardial infarction; uncompensated heart failure; and taking other drugs that increase QT interval. In some embodiments, the methods can include selecting and/or administering/providing ibogaine to a patient that lacks one more of such criteria.

In one embodiment, this invention relates to pre-screening a patient to determine if the patient is at risk for prolongation of the QT interval beyond a safe level. In one embodiment, a patient at risk for prolongation of the QT interval beyond a safe level is not administered ibogaine, an ibogaine derivative, or a pharmaceutically acceptable salt and/or solvate thereof. In one embodiment, a patient at risk for prolongation of the QT interval beyond a safe level is administered ibogaine, an ibogaine derivative, or a pharmaceutically acceptable salt and/or solvate thereof at a limited dosage.

In one embodiment, this invention relates to monitoring a patient who is administered a therapeutic dose of ibogaine, an ibogaine derivative, or a pharmaceutically acceptable salt and/or solvate thereof. In one embodiment, the dose of ibogaine, an ibogaine derivative, or a pharmaceutically acceptable salt and/or solvate thereof is reduced if the patient has one or more adverse side effects. In one embodiment, the ibogaine, an ibogaine derivative, or a pharmaceutically acceptable salt and/or solvate thereof treatment is discontinued if the patient has one or more adverse side effects. In one embodiment, the adverse side effect is a QT interval that is prolonged beyond a safe level. The determination of a safe level of prolongation is within the skill of a qualified clinician.

Kit of Parts

One aspect of this invention is directed to a kit of parts for the treatment of pain and/or symptoms of post-acute and/or chronic pain in a patient, wherein the kit comprises a composition comprising ibogaine, an ibogaine derivative, or a pharmaceutically acceptable salt and/or solvate thereof and a means for administering the composition to a patient in need thereof. The means for administration to a patient can include, for example, any combination of ibogaine, an ibogaine derivative, or a pharmaceutically acceptable salt and/or solvate thereof, a transdermal patch, a syringe, a needle, an IV bag comprising the composition, a vial comprising the composition, an inhaler comprising the composition, etc. In one embodiment, the kit of parts further comprises instructions for dosing and/or administration of the composition.

In some aspects, the invention is directed to a kit of parts for administration of ibogaine, an ibogaine derivative, or a pharmaceutically acceptable salt and/or solvate thereof, the kit comprising multiple delivery vehicles, wherein each delivery vehicle contains a discrete amount of ibogaine, an ibogaine derivative, or a pharmaceutically acceptable salt and/or solvate thereof and further wherein each delivery vehicle is identified by the amount of ibogaine, an ibogaine derivative, or a pharmaceutically acceptable salt and/or solvate thereof provided therein; and optionally further comprising a dosing treatment schedule in a readable medium. In some embodiments, the dosing treatment schedule includes the amount of ibogaine, an ibogaine derivative, or a pharmaceutically acceptable salt and/or solvate thereof required to achieve each average serum level is provided. In some embodiments, the kit of parts includes a dosing treatment schedule that provides an attending clinician the ability to select a dosing regimen of ibogaine, an ibogaine derivative, or a pharmaceutically acceptable salt and/or solvate thereof based on the sex of the patient, mass of the patient, and the serum level that the clinician desires to achieve. In some embodiments, the dosing treatment schedule further provides information corresponding to the volume of blood in a patient based upon weight (or mass) and sex of the patient. In an embodiment, the storage medium can include an accompanying pamphlet or similar written information that accompanies the unit dose form in the kit. In an embodiment, the storage medium can include electronic, optical, or other data storage, such as a non-volatile memory, for example, to store a digitally-encoded machine-readable representation of such information.

The term "delivery vehicle" as used herein refers to any formulation that can be used for administration of ibogaine, an ibogaine derivative, or a pharmaceutically acceptable salt and/or solvate thereof to a patient. Non-limiting, exemplary delivery vehicles include caplets, pills, capsules, tablets, powder, liquid, or any other form by which the drug can be administered. Delivery vehicles may be intended for administration by oral, inhaled, injected, or any other means.

The term "readable medium" as used herein refers to a representation of data that can be read, for example, by a human or by a machine. Non-limiting examples of human-readable formats include pamphlets, inserts, or other written forms. Non-limiting examples of machine-readable formats include any mechanism that provides (i.e., stores and/or transmits) information in a form readable by a machine (e.g., a computer, tablet, and/or smartphone). For example, a machine-readable medium includes read-only memory (ROM); random access memory (RAM); magnetic disk storage media; optical storage media; and flash memory devices. In one embodiment, the machine-readable medium is a CD-ROM. In one embodiment, the machine-readable medium is a USB drive. In one embodiment, the machine-readable medium is a Quick Response Code (QR Code) or other matrix barcode.

In some aspects, the machine-readable medium comprises software that contains information regarding dosing schedules for the unit dose form of ibogaine, an ibogaine derivative, or a pharmaceutically acceptable salt and/or solvate thereof and optionally other drug information. In some embodiments, the software may be interactive, such that the attending clinician or other medical professional can enter patient information. In a non-limiting example, the medical professional may enter the weight and sex of the patient to be treated, and the software program provides a recommended dosing regimen based on the information entered. The amount and timing of ibogaine, an ibogaine derivative, or a pharmaceutically acceptable salt and/or solvate thereof recommended to be delivered will be within the dosages that result in the serum concentrations as provided herein.

In some embodiments, the kit of parts comprises multiple delivery vehicles in a variety of dosing options. For example, the kit of parts may comprise pills or tablets in multiple dosages, such as 240 mg, 120 mg, 90 mg, 60 mg, 30 mg, 20 mg, and/or 10 mg of ibogaine, an ibogaine derivative, or a pharmaceutically acceptable salt and/or solvate thereof per pill. Each pill is labeled such that the medical professional and/or patient can easily distinguish different dosages. Labeling may be based on printing or embossing on the pill, shape of the pill, color of pill, the location of the pill in a separate, labeled compartment within the kit, and/or any other distinguishing features of the pill. In some embodiments, all of the delivery vehicles within a kit are intended for one patient. In some embodiments, the delivery vehicles within a kit are intended for multiple patients.

One aspect of this invention is directed to a kit of parts for the treatment of pain, including symptoms of post-acute and chronic pain in a patient, wherein the kit comprises a unit dose form of ibogaine, an ibogaine derivative, or a pharmaceutically acceptable salt and/or solvate thereof. The unit dose form provides a patient with an average serum level of ibogaine, an ibogaine derivative, or a pharmaceutically acceptable salt and/or solvate thereof of from about 50 ng/mL to about 800 ng/mL or about 60 ng/mL to about 800 ng/mL.

In some embodiments, the unit dose form comprises one or multiple dosages to be administered periodically, such as once, twice, three time, four times or five time daily with ibogaine, an ibogaine derivative, or a pharmaceutically acceptable salt and/or solvate thereof or its prodrug. In some embodiments, the administration is once daily, or once every second day, once every third day, three times a week, twice a week, or once a week. The dosage and frequency of the administration depends on criteria including the route of administration, content of composition, age and body weight of the patient, condition of the patient, sex of the patient, without limitation, as well as by the severity of the addiction. Determination of the unit dose form providing a dosage and frequency suitable for a given patient can readily be made by a qualified clinician.

These dose ranges may be achieved by transdermal, oral, or parenteral administration of ibogaine, an ibogaine derivative, or a pharmaceutically acceptable salt and/or solvate thereof or a pharmaceutically acceptable salt or solvate thereof in unit dose form. Such unit dose form may conveniently be provided in transdermal patch, tablet, caplet, liquid or capsule form. In certain embodiments, the ibogaine, an ibogaine derivative, or a pharmaceutically acceptable salt and/or solvate thereof is provided as ibogaine HCl, with dosages reported as the amount of free base ibogaine, an ibogaine derivative, or a pharmaceutically acceptable salt and/or solvate thereof. In some embodiments, the ibogaine HCl is provided in hard gelatin capsules containing only ibogaine HCl with no excipients. In some embodiments, ibogaine, an ibogaine derivative, or a pharmaceutically acceptable salt and/or solvate thereof is provided in saline for intravenous administration.

Formulations

This invention further relates to pharmaceutically acceptable formulations comprising a unit dose of ibogaine, an ibogaine derivative, or a pharmaceutically acceptable salt and/or solvate thereof, wherein the amount of ibogaine, an ibogaine derivative, or a pharmaceutically acceptable salt and/or solvate thereof is sufficient to provide an average serum concentration of about 50 ng/mL to about 850 ng/mL when administered to a patient. In a preferred embodiment, the amount of ibogaine is sufficient to provide an average serum concentration of about 50 ng/mL to about 400 ng/mL when administered to a patient.

In some embodiments, the unit dose of ibogaine, an ibogaine derivative, or a pharmaceutically acceptable salt and/or solvate thereof is administered in one or more dosings.

In one embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 800 ng/mL or about 60 ng/mL to about 800 ng/mL. In one embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 700 ng/mL or about 60 ng/mL to about 700 ng/mL. In one embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 600 ng/mL, or about 60 ng/mL to about 600 ng/mL. In a preferred embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 500 ng/mL, or about 60 ng/mL to about 500 ng/mL. In one embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 400 ng/mL, or about 60 ng/mL to about 400 ng/mL. In one embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 300 ng/mL, or about 60 ng/mL to about 300 ng/mL. In one embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 200 ng/mL, or about 60 ng/mL to about 200 ng/mL. In one embodiment, the amount of ibogaine, an ibogaine derivative, or a pharmaceutically acceptable salt and/or solvate thereof is sufficient to provide an average serum concentration of ibogaine, an ibogaine derivative, or a pharmaceutically acceptable salt and/or solvate thereof from about 50 ng/mL to about 100 ng/mL, or about 60 ng/mL to about 100 ng/mL. The ranges include both extremes as well as any subranges between.

EXAMPLES

The following Examples are intended to further illustrate certain embodiments of the disclosure and are not intended to limit its scope.

Example 1

Use of Ibogaine to Treat Chronic Pain in Humans

Six patients experiencing chronic pain are screened and selected to receive administration of ibogaine. Four patients intranasally absorb a milligram amount of ibogaine hydrochloride and the remaining two patients receive a placebo. The level of pain and pain relief are measured.

What is claimed is:

1. A method for treating pain in a patient, comprising administering to the patient a dosage of a compound selected from ibogaine, an ibogaine derivative, and a pharmaceutically acceptable salt and/or solvate thereof, wherein the ibogaine derivative is selected from the group consisting of coronaridine, voacangine, 18-methoxy coronaridine, 2-methoxyethyl-18-methoxycoronaridinate, 18-methylaminocoronaridine, 16-hydroxymethyl-18-hydroxyibogaline, 16-hydroxymethyl-18-methoxylibogaline, 16-ethoxycarbonyl-18-hydroxyibogaline laurate, and 16-ethoxycarbonyl-18-hydroxyibogaline methoxyethoxymethyl ether, wherein the administering provides an average serum concentration of less than about 250 ng/mL of the compound, said concentration being sufficient to alleviate and/or inhibit said pain while maintaining a QT interval of less than about 500 ms during said treatment.

2. The method of claim 1, wherein the ibogaine, the ibogaine derivative, or the pharmaceutically acceptable salt and/or solvate thereof is administered as a single dose or multiple doses.

3. The method of claim 1, wherein the aggregate dosage of ibogaine, the ibogaine derivative, or the pharmaceutically acceptable salt and/or solvate thereof is selected from the group consisting of from about 1.3 mg/kg to about 4 mg/kg per day, about 1.5 mg/kg to about 3 mg/kg per day, about 2 mg/kg to about 4 mg/kg per day, from about 2 mg/kg to about 3 mg/kg per day, and about 2 mg/kg per day.

4. The method of claim 1, wherein the dosage of ibogaine, the ibogaine derivative, or the pharmaceutically acceptable salt and/or solvate thereof provides an average serum concentration of about 50 ng/mL to about 200 ng/mL.

5. The method of claim 1, wherein the ibogaine derivative is selected from the group consisting of coronaridine, ibogamine, voacangine, 18-methoxycoronaridine, 2-Methoxyethyl-18-methoxycoronaridinate, and 18-Methylaminocoronaridine.

6. The method of claim 1, wherein the ibogaine derivative is selected from the group consisting of 16-hydroxymethyl-18-hydroxyibogaline, 16-hydroxymethyl-18-methoxyibogaline, 16-ethoxycarbonyl-18-hydroxyibogaline laurate, and 16-ethoxycarbonyl-18-hydroxyibogaline methoxyethoxymethyl ether.

* * * * *